US007858828B2

(12) United States Patent
Khachik et al.

(10) Patent No.: US 7,858,828 B2
(45) Date of Patent: Dec. 28, 2010

(54) PROCESS FOR SYNTHESIS OF (3R,3'R,6'R)-LUTEIN AND ITS STEREOISOMERS

(75) Inventors: Frederick Khachik, Rockville, MD (US); An-Ni Chang, Greenbelt, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 12/410,794

(22) Filed: Mar. 25, 2009

(65) Prior Publication Data

US 2009/0264681 A1 Oct. 22, 2009

Related U.S. Application Data

(60) Provisional application No. 61/039,576, filed on Mar. 26, 2008.

(51) Int. Cl.
C07C 45/27 (2006.01)
C07C 29/38 (2006.01)

(52) U.S. Cl. ................... 568/343; 568/344; 568/356; 568/816

(58) Field of Classification Search ............... 568/343, 568/344, 356, 816
See application file for complete search history.

(56) References Cited

U.S. PATENT DOCUMENTS 3,607,942 A * 9/1971 Rowland ............ 568/344
4,393,243 A * 7/1983 Lohri ............... 568/344
2009/0238933 A1 9/2009 Khachik

OTHER PUBLICATIONS

U.S. Appl. No. 12/484,703, Khachik and Chang.
Adams, C., "Sodium Borohydride: Tartaric Acid. A Novel and Facile Reducing Agent for Cyclic Ketones", *Synthetic Communications*, 14:955-959 (1984), Taylor & Francis Group Ltd., Oxford, UK.
Andriamialisoa, Z., et al., "New Preparation of an Important Synthon for Vitamin A Synthesis", *Tetrahedron Letters*, 34:8091-8092 (1993), Pergamon Press, Great Britain, UK.
Bernhard, V.K., "157. Synthese von optisch aktiven, natürlichen Carotinoiden und strukturell verwandten Naturprodukten VIII. Synthese von (3S,3'S)-7,8,7',8'-Tetradehydroastaxanthin und (3S,3'S)-7-8-Didehydroastaxanthin (Asterinsäure)¹)," *Helvetica Chimica Acta*, 63:1473-1490 (1980), Verlag Helvetica Chimica Acta, Zürich, Switzerland.
Cordes, D.B., et al., "Asymmetric Reduction of Ketones Under Mild Conditions Using NaBH₄ and TarB-NO₂: An Efficient and Unusual Chiral Acyloxyborohydride Reducing System," *Eur. J. Org. Chem.*, 24:5289-5295 (2005), Wiley-VCH Verlag GmbH & Co. KgaA, Weinheim, Germany.
Haag, A. and Eugster, C.H., "199. Synthesen von optisch aktiven Carotinoiden mit einer (R)-4-Hydroxy-β-Endgruppe," *Helvetica Chimica Acta*, 68:1897-1906 (1985), Verlag Helvetica Chimica Acta, Zürich, Switzerland.

Haugan, J.A., "Total Synthesis of $C_{31}$-Methyl Ketone Apocarotenoids: Sintaxanthin and (3R)-3-Hydroxysintaxanthin," *Acta Chemica Scandinavia*, 48:657-664 (1994), Munksgaard International Publishers Ltd., Copenhagen K, Denmark.
Hirao, A., et al., "Asymmetric Reduction of Aromatic Ketones with Chirally Modified Reagents Prepared from Sodium Borohydride and Optically Active Acids in the Presence of 1,2:5,6-Di-O-isopropylidene-α-D-glucofuranose," *Agric. Biol. Chem.*, 45:693-697 (1981), The Agricultural Chemical Society of Japan, Tokyo, Japan.
Imai, H., et al., "Probing for the Threshold Energy for Visual Transduction: Red-Shifted Visual Pigment Analogs from 3-Methoxy-3-Dehydroretinal and Related Compounds," *Photochemistry and Photobiology*, 70:111-115 (1999), The American Society for Photobiology, Lawrence, Kansas, USA.
Marwah, P., et al., "An economical and green approach for the oxidation of olefins to enones," *Green Chem.*, 6:570-577 (2004), Royal Society of Chemistry, Cambridge, UK.
Mayer, H. and Rüttmann, A., "153. Synthese von optisch aktiven, natürlichen Carotinoiden und strukturell verwandten Naturprodukten IV. Synthese von (3R,3'R,6'R)-Lutein," *Helvetica Chimica Acta*, 63:1451-1455 (1980), Verlag Helvetica Chimica Acta AG, Zürich, Switzerland.
Prelog, V. and Osgan, M., "123. Untersuchungen über Organextrakte und Harn. 23. Mitteilung. Über das 5-Oxo-α-jonon und über die Synthese der Diole A und B, des Ketons C und des Diketons D aus dem Ham von trächtigen Stuten," *Helvetica Chimica Acta*, 35:986-992 (1952), Verlag Helvetica Chimica Acta, Zürich, Switzerland.
Soukup, M., et al., "88. Technical Procedures for the Syntheses of Carotenoids and Related Compounds from 6-Oxo-isophorone: Syntheses of (3R,3'R)-Zeaxanthin," *Helvetica Chimica Acta*, 73:868-873 (1990), Verlag Helvetica Chimica Acta, Zürich, Switzerland.
Soukup, M., et al.,"Part II: Strategies for Building the Carbon Skeleton," *Carotenoids* 2:7-14 (1995), vol. 2: Synthesis, Birkhauser Verlag, Basel, Switzerland.
Widmer, V.E., et al., "88. Technische Verfahren zur Synthese von Carotinoiden und verwandten Verbindungen aus 6-Oxo-isophoron. VI. Synthese von Rhodoxanthin und (3RS,3'RS)-Zeaxanthin; Zugänge zur $C_{15}$-Ringkomponente über 3-Oxo-jonon-Derivate," *Helvetica Chimica Acta*, 65:944-957 (1982), Verlag Helvetica Chimica Acta AG, Zürich, Switzerland.

(Continued)

*Primary Examiner*—Sikarl A Witherspoon
(74) *Attorney, Agent, or Firm*—Sterne, Kessler, Goldstein & Fox P.L.L.C.

(57) ABSTRACT

(3R,3'R,6'R)-Lutein and (3R,3'R)-zeaxanthin are two dietary carotenoids that are present in most fruits and vegetables commonly consumed in the US. These carotenoids accumulate in the human plasma, major organs, and ocular tissues. In the past decade, numerous epidemiological and experimental studies have shown that lutein and zeaxanthin play an important role in the prevention of age-related macular degeneration (AMD) that is the leading cause of blindness in the U.S. and Western World. The invention provides a process for the synthesis of (3R,3'R,6'R)-lutein and its stereoisomers from commercially available (rac)-α-ionone by a $C_{15}+C_{10}+C_{15}$ coupling strategy. In addition, the present invention also provides access to the precursors of optically active carotenoids with 3-hydroxy-ε-end group that are otherwise difficult to synthesize. The process developed for the synthesis of lutein and its stereoisomers is straightforward and has potential for commercialization.

60 Claims, 6 Drawing Sheets

OTHER PUBLICATIONS

Widmer, E., et al., "87. Technical Procedures for the Syntheses of Carotenoids and Related Compounds from 6-Oxo-isophorone: Syntheses of (3R,3'R)-Zeaxanthin," *Helvetica Chimica Acta*, 73:861-867 (1990), Verlag Helvetica Chimica Acta, Zürich, Switzerland.

Yamano, Y., et al., "Synthesis of Zeaxanthin- And Cryptoxanthin-β-D-Glucopyranosides," *Heterocycles* 52:141-146 (2000), The Japanese Institute of Heterocyclic Chemistry, Tokyo, Japan.

Yang, M., et al., "$CaCl_2$- or $MgCl_2$-catalyzed allylic oxidations of ionone-like dienes," *Synlett*, 16: 2617-2620 (2006), Thieme, Stuttgart, Germany.

Yatagai, M. and Ohnuki, T., "Asymmetric Reduction of Functionalized Ketones with a Sodium Borohydride-(L)-Tartaric Acid System," *J. Chem. Soc. Perkin Trans.*, 1:1826-1828 (1990), The Royal Society of Chemistry, Cambridge, England, UK.

Young, W.G., et al., "Polyenes. I. The Synthesis and Absorption Spectra of the Ionylideneacetones and Related Compounds," *J. Am. Chem. Soc.*, 66:520-524 (1944), The American Chemical Society, Cambridge, MA, USA.

Yu, J.-Q. and Corey, E.J., "Diverse Pathways for the Palladium (II)-Mediated Oxidation of Olefins by *tert*-Butylhydroperoxide," *Organic Letters*, 4:2727-2730 (2002), The American Chemical Society, Washington, DC, USA.

Biosis Previews (R) Database, Biosis No. 19522600027727, Prelog, V. and Osgan, M., "Untersuchugen über Organextrakte und Harn. 23. Mitteilung. Über das 5-Oxo-α-jonon und über die Synthese der Diole A und B, des Ketons C und des Diketons D aus dem Harn von trächtigen Stuten," *Helvetica Chimica Acta*, 35:986-992 (1952), Verlag Helvetica Chimica Acta, Zürich, Switzerland.

* cited by examiner

*Carotenoid numbering system has been used for all end-group precursors of luteins.

a) (EtO)$_2$P(O)CH$_2$CN or (iso-PrO)$_2$P(O)CH$_2$CN/NaH, TBME or THF or NaOMe/MeOH;
b) tert-BuOOH (TBHP), bleach (5.25% NaOCl), CH$_3$CN, -5 to 0°C or TBHP, K$_2$CO$_3$, Pd/C, CH$_2$Cl$_2$, 0°C to R.T.; c) CH$_2$(CN)CO$_2$H, cyclohexylamine, 80-85°C, 3.5 h; d) KBH(sec-C$_4$H$_9$)$_3$ (K-SELECTRIDE™) or NaBH(sec-C$_4$H$_9$)$_3$ (N-SELECTRIDE™), TBME or THF, -30°C. *Carotenoid numbering system has been used for all end-group precursors of luteins.

*Carotenoid numbering system has been used for all end-group precursors of luteins.

*Carotenoid numbering system has been used for $C_{18}$-ketones 27 and 28.

PROCESS FOR SYNTHESIS OF (3R,3'R,6'R)-LUTEIN AND ITS STEREOISOMERS

BACKGROUND OF THE INVENTION

1. Field of the Invention

The invention is in the field of organic chemistry. The invention relates to a process for the synthesis of (3R,3'R, 6'R)-lutein and its stereoisomers from commercially available (rac)-α-ionone by a $C_{15}+C_{10}+C_{15}$ coupling strategy. Employing this methodology, (3R,3'R,6'R)-lutein (dietary), (3R,3'S,6'S)-lutein, (3R,3'S,6'R)-lutein (3'-epilutein), and (3R,3'R,6'S)-lutein have been prepared. Based on this strategy, the other 4 stereoisomers of lutein that are enantiomeric to the above lutein isomers can also be prepared. These are: (3S,3'S,6'S)-lutein, (3S,3'R,6'R)-lutein, (3S,3'R,6'S)-lutein, and (3S,3'S,6'R)-lutein.

macular degeneration (AMD) that is the leading cause of blindness in the U.S. and Western World. While (3R,3'R)-zeaxanthin has been commercially available by total synthesis for more than two decades, the industrial production of (3R,3'R,6'R)-lutein by chemical synthesis has not yet materialized. Consequently, this carotenoid is commercially produced from saponified extracts of marigold flowers. The major difficulty with the total synthesis of (3R,3'R,6'R)-lutein is due to the presence of 3 stereogenic centers at C3, C3', and C6' positions in this carotenoid that can result in 8 possible stereoisomers. The chemical structures of 4 of these stereoisomers are shown in Scheme 1. Among these, dietary (3R, 3'R,6'R)-lutein (1) and one of its metabolites, (3R,3'S,6'R)-lutein (3'-epilutein) (3), have been detected in human plasma and tissues. The other 4 stereoisomers of lutein (structures not shown), are those in which the configuration at C3 position is S while the stereochemistry at C3' and C6' remains the same as those lutein isomers shown in Scheme 1.

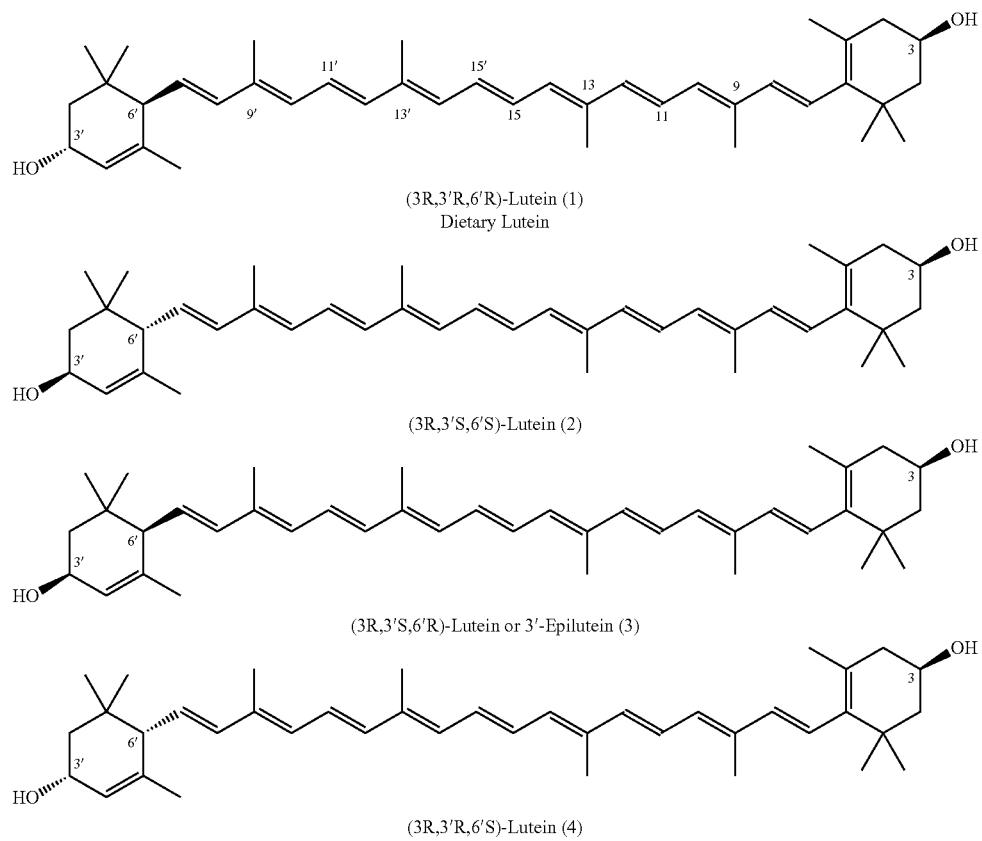

SCHEME 1
The chemical structure of dietary (3R,3'R,6'R)-lutein and three of its stereoisomers.

(3R,3'R,6'R)-Lutein (1)
Dietary Lutein (3R,3'S,6'S)-Lutein (2)

(3R,3'S,6'R)-Lutein or 3'-Epilutein (3)

(3R,3'R,6'S)-Lutein (4)

2. Background Art (3R,3'R,6'R)-Lutein and (3R,3'R)-zeaxanthin are two dietary carotenoids that are present in most fruits and vegetables commonly consumed in the US. These carotenoids accumulate in the human plasma, major organs, and ocular tissues (macula, retinal pigment epithelium (RPE), ciliary body, iris, lens). In the past decade, numerous epidemiological and experimental studies have shown that lutein and zeaxanthin play an important role in the prevention of age-related To date, the only total synthesis of dietary (3R,3'R,6'R)-lutein (1) has been reported by Mayer and Rüttimann (*Helv. Chim. Acta*, 1980, 63:1451-55) and is based on the $C_{15}+C_{10}+C_{15}$ strategy as shown in FIG. 1. According to this methodology, the $C_{15}$-Wittig salt, (3R)-3-hydroxy-(β-ionylideneethyl) triphenylphosphonium chloride (5), is reacted with one equiv. of 2,7-dimthylocta-2,4,6-triene-1,8-dial ($C_{10}$-dialdehyde) to give a $C_{25}$-aldehyde, (3R)-3-hydroxy-12'-apo-β-caroten-12'-al. Both starting materials for this reaction are commercially available and have been employed in the total synthesis of (3R,3'R)-zeaxanthin by the same group. To complete the synthesis of (3R,3'R,6'R)-lutein, Mayer and Rüttimann prepared (3R,6R)-3-acetoxy-α-ionylideneethyl)triphenylphosphonium chloride in 8 steps from (S)-4-hydroxy-2,6,6-trimethyl-2-cyclohexene-1-one in an overall yield of 6.3%. In the final step of this synthesis, these investigators reacted the $C_{25}$-aldehyde with (3R,6R)-3-acetoxy-α-ionylideneethyl)triphenylphosphonium chloride or bromide to obtain (3R,3'R,6'R)-lutein in 25% yield. Therefore the overall yield for the reported total synthesis of lutein according to this methodology was about 1.6%.

The total synthesis of lutein described in FIG. 1, involves numerous steps and results in a poor overall yield. Consequently, this synthetic approach does not provide an efficient and economically viable route for industrial production of (3R,3'R,6'R)-lutein (1). Therefore, the present invention was developed to provide a more practical route to 1 by employing a divergent synthetic strategy that could be simultaneously applied to the synthesis of other stereoisomers of this carotenoid such as (3R,3'S,6'S)-lutein (2), (3R,3'S,6'R)-lutein (3), and (3R,3'R,6'S)-lutein (4). In addition, this synthetic strategy also provides access to the precursors of optically active carotenoids with 3-hydroxy-ε-end group that are otherwise difficult to prepare.

SUMMARY OF THE INVENTION

Despite the difficulties encountered with the synthesis of (3R,3'R,6'R)-lutein, the $C_{15}+C_{10}+C_{15}$ building block strategy for the synthesis of carotenoids is, in most cases, the method of choice. This is because the formation of the double bonds at 11 and 11' positions yields predominantly the all-E (trans)-isomer (Soukup, M; Spurr, P; Widmer, E. In: *Carotenoids, Volume 2: Synthesis*, Britton, G; Liaaen-Jensen, S; Pfander, H. Eds.; Birkhäuser: Basel, 1995, pp 7-14). Therefore, this strategy has also been employed in the present invention. However, because of the poor overall yield in the reported synthetic strategy by Mayer and Rüttimann, we employed entirely different $C_{15}$- and $C_{10}$-building blocks. This was because (3R,6R)-3-acetoxy-(α-ionylideneethyl)triphenylphosphonium halide that was used in the final step of the reported synthesis of lutein appeared to be difficult to synthesize due to the presence of an acid-sensitive allylic hydroxyl group in the precursor to this Wittig salt (FIG. 1). In addition, the olefination of (3R)-3-hydroxy-12'-apo-β-caroten-12'-al ($C_{25}$-aldehyde) with this Wittig salt according to Mayer and Rüttimann only gave 25% yield of lutein.

The retrosynthetic pathways employed in the present invention is shown in FIG. 2. In contrast to the reported synthesis of lutein, the final step of our synthesis involved the elongation of the optically pure $C_{25}$-hydroxyaldehydes 6-9 with the Wittig salt 5 that could be readily prepared according to the known processes (Widmer et al., *Helv. Chim. Acta*, 1990, 73: 861-867; Soukup et al., *Helv. Chim. Acta*, 1990, 73: 868-873). We rationalized that the optically pure $C_{25}$-hydroxyaldehydes 6-9 could be prepared from deprotection of their corresponding dimethylacetals 10-13 under mild acidic conditions without epimerization of their allylic hydroxyl groups at C3. These acetals could in turn be prepared from the reaction of protected Wittig salt 14 with the optically pure $C_{15}$-hydroxyaldehydes 15-18 with the required stereochemistry at C3 and C6. The protected Wittig salt 14 was readily accessible according to published methods (Bernhard et al., *Helv. Chim. Acta*, 1980, 63:1473-1490; Haugen, *Acta Chimica Scand*. 1994, 48: 657-664). The application of this Wittig salt in the synthesis of unsymmetrical carotenoids with sensitive end-groups has been well documented in the literature (Bernhard et al., *Helv. Chim. Acta*, 1980, 63:1473-1490; Haag and Eugster, *Helv. Chim. Acta*, 1985, 68:1897-1906; Yamano et al. *Heterocycles*, 2000, 52: 141-146). However, this building block has not been employed in the synthesis of lutein or its precursors. The $C_{15}$-hydroxynitriles 19-22 as a racemic mixture or with the appropriate stereochemistry at C3 and C6 could serve as the precursors to $C_{15}$-hydroxyaldehydes 15-18. (7E,9E)-3-Keto-α-ionylideneacetonitrile (23a) and its (7E,9Z)-isomer (23b), prepared from nitriles 24a and 24b, could be transformed into $C_{15}$-hydroxynitriles 19-22. However the (7E,9E)-isomer (23a) would be preferable since this would avoid the difficulties associated with the separation of optically active E/Z-isomers throughout our entire synthetic strategy.

The commercially available and inexpensive (rac)-α-ionone was selected as the starting material for the synthesis of nitriles 24a/24b that have been previously synthesized according to known methods. However, we had to develop a methodology that could provide 24a as a single isomer and transform this nitrile into 23a without stereisomerization. Other challenges with our synthetic approach involved separation of $C_{15}$-hydroxyaldehydes 15-18 and their precursors in high optical purity and maintaining their integrity throughout the total synthesis of luteins 1-4. It should be noted that all of the precursors to luteins 1-4 that are shown in our retrosynthetic pathways in FIG. 2, are reported here for the first time and have not been synthesized previously. This is with the exception of nitriles 24a/24b and ketonitriles 23a/23b that have been prepared as a mixture of E/Z isomers by entirely different processes than those developed in the present invention.

One of the key starting materials in the retrosynthetic pathways shown in FIG. 2 is (rac)-3-keto-α-ionylideneacetonitrile which had to be preferentially synthesized as the (7E,9E)-isomer (23a) at the expense of its (7E,9Z)-isomer (23b). This is because when (rac)-ketonitrile 23a is reduced in the following step, a new stereogenic center at C3 is generated that results in the formation of four stereoisomers, namely, (rac)-hydroxynitriles 19-22. Consequently, the reduction of a mixture of ketonitriles 23a and 23b, could afford as many as 8 stereoisomeric hydroxynitriles which would be difficult to separate in high optically purity. Therefore, the initial goal of this invention was to explore the possible routes by which (rac)-α-ionone could be transformed into ketonitrile 23a. Three synthetic routes were employed for transformation of (rac)-α-ionone to ketonitrile 23a that served as a precursor to $C_{15}$-hydroxynitriles 19-22 (FIG. 3). According to the first route, Horner-Wadsworth-Emmons (HWE) reaction of (rac)-α-ionone with diethyl cyanomethylphosphonate or diisopropyl cyanomethylphosphonate gave (rac)-α-ionylideneacetonitriles 24a (75%) and 24b (25%) as a mixture of isomers that were converted to a mixture of 23a (75%) and 23b (25%) by allylic oxidation.

However, a more effective strategy (Route 2, FIG. 3) was developed that involved Knoevenagel condensation of (rac)-α-ionone with cyanoacetic acid to afford 24a (92%) as the major isomer and 24b (8%) as the minor isomer. When a mixture of 24a (92%) and 24b (8%) was subjected to allylic oxidation, 23a (92%) and 23b (8%) were obtained without E/Z-isomerization and the (7E,9E)-isomer (23a) could be crystallized from the mixture.

In an alternative approach (Route 3, FIG. 3), (rac)-α-ionone was first converted to (rac)-3-keto-α-ionone by allylic oxidation followed by HWE olefination with diethyl cyanomethylphosphonate to yield a mixture of 23a (75%) and 23b (25%). Consequently, among these three strategies, Route 2 that involved Knoevenagel reaction of (rac)-α-ionone with cyanoacetic acid and provided 23a in high stereoselectivity was the preferred route. Reduction of the ketonitrile 23a with a number of reducing agents provided a mixture of four stereoisomeric $C_{15}$-hydroxynitriles 19-22. Among the reducing agents employed, potassium tri-sec-butylborohydride (K-SELECTRIDE™) at −30° C. in TBME or THF produced the greatest amount of the hydroxynitriles 19 and 20 (86%) relative to the hydroxynitriles 21 and 22 (14%). However, when $BH_3$/(R)-2-methyl-CBS-oxazaborolidine was used as the reducing agent, this stereoselectivity was reversed and hydroxynitriles 21 and 22 (86%) were the major products and hydroxynitriles 19 and 20 (14%) were the minor products. The separation of hydroxynitriles 19 and 20 from hydroxynitriles 21 and 22 by column chromatography proved to be challenging. However, this was accomplished by subjecting these nitriles to two successive column chromatography separations. In the next step, enzyme-mediated acylation with lipase AK (*Pseudomonas fluorescens*) or lipase PS (*Pseudomonas cepacia*) was employed to separate the enantiomeric hydroxyaldehydes 21 from 22. However, these enzymatic separations resulted in poor enantiomeric excess (ee) and the partially resolved enantiomers had to be subjected to a second enzymatic acylation to provide the optically pure hydroxynitriles 19-22. Consequently, this approach was not appealing due to the need for repeated column chromatography and enzyme-mediated acylation of racemic nitriles. Therefore, a more robust strategy was developed that eliminated these difficulties and afforded the hydroxyaldehydes 15-18 in excellent optical purities (FIG. 4). As shown in FIG.

ated acylation with lipase AK (*Pseudomonas fluorescens*) in the presence of vinyl acetate in refluxing pentane. While hydroxyaldehyde 17 underwent acylation to acetoxyaldehyde 26, hydroxyaldehyde 18 remained unchanged; these were then separated by column chromatography. Saponification of acetoxyaldehyde 26 with KOH/MeOH at 0° C. afforded hydroxyaldehyde 17. Employing this methodology, hydroxyaldehydes 17 and 18 were obtained in enantiomeric excess (ee) of 91% and 92%, respectively. Therefore, all four $C_{15}$-hydroxyaldehydes 15-18 became accessible in excellent optical purity and were utilized in the synthesis of luteins 1-4 according to the synthetic pathways shown in FIG. 5.

The Wittig reaction of optically pure $C_{15}$-hydroxyaldehydes 15-18 with the required stereochemistry at C3 and C6 with the protected Wittig salt 14 afforded 3-hydroxy-12'-apo-ε-caroten-12'-al dimethylacetals 10-13 (protected $C_{25}$-aldehydes) in yields ranging from 75-85%. As part of the work-up of the same reaction, the protecting group in acetals 10-13 was removed under mild acidic conditions without epimerization at C3 to afford $C_{25}$-hydroxyaldehydes 6-9, respectively. In the final step of the synthesis of luteins, aldehydes 6-9 were allowed to react with the Wittig salt 5 to yield luteins 1-4 in yields ranging from 65-74%. Therefore, according to the present invention, luteins 1 and 2 were each prepared in an overall yield of 21% based on the optically active $C_{15}$-hydroxyaldehydes 15+16. Similarly, luteins 3 and 4 were prepared in overall yields of 16% and 18%, respectively. These $C_{15}$-hydroxyaldehydes served as the key starting material in our synthetic strategy.

In one embodiment of the present invention, a compound having the Formula (I):

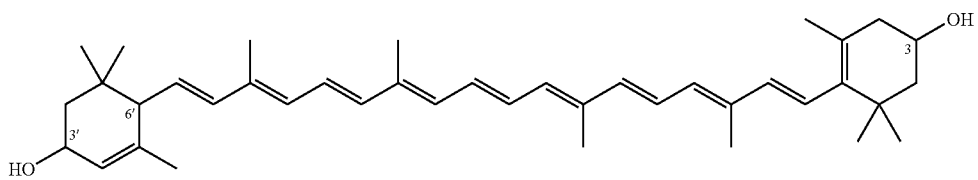

4, the hydroxynitriles 19-22 were first transformed into a racemic mixture of hydroxyaldehydes 15-18 by DIBAL-H and the mixture was then subjected to column chromatography. Unlike hydroxynitriles, hydroxyaldehydes 15+16 were readily separated from hydroxyaldehydes 17+18 by column chromatography. In an alternative one-pot reaction, ketonitrile 23a was reduced to hydroxynitriles 19-22 with K-SELECTRIDE™ followed by the reduction with DIBAL-H to afford hydroxyaldehydes 15-18 in one convenient step.

In the following step, enzyme-mediated acylation was employed to resolve the racemic mixture of hydroxyaldehydes 15 and 16. Therefore, when a mixture of hydroxyaldehydes 15 and 16 was subjected to enzymatic acylation with lipase AK (*Pseudomonas fluorescens*) in the presence of vinyl acetate in refluxing pentane (35-36° C.), hydroxyaldehyde 16 was acylated to acetoxyaldehyde 25 within 48 h, while hydroxyaldehyde 15 remained unchanged (FIG. 4). Acetoxyaldehydes 25 was then readily separated from hydroxyaldehyde 15 by column chromatography. Acetoxyaldehyde 25 was saponified with KOH/MeOH at 0° C. to yield hydroxyaldehyde 16. According to this strategy, hydroxyaldehydes 15 and 16 were obtained in enantiomeric excess (ee) of 94% and 93%, respectively.

Similarly, the resolution of a racemic mixture of hydroxyaldehydes 17 and 18 was accomplished with enzyme-mediis synthesized by reacting a compound having the Formula (II):

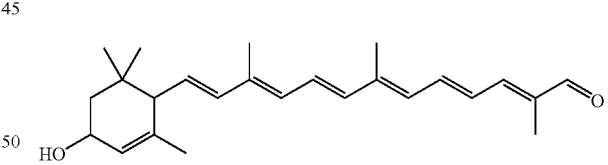

with a compound having the Formula (III):

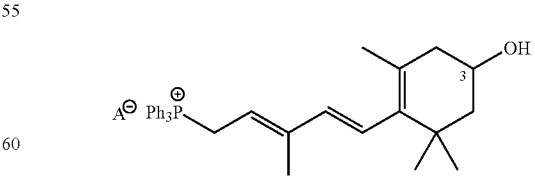

via Wittig coupling, wherein $A^{\ominus}$ is an anionic counterion such as $Cl^-$, $Br^-$ or $I^-$. In some embodiments, the compound of Formula (I) is (3R,3'R,6'R)-lutein, (3R,3'S,6'S)-lutein, (3R, 3'S,6'R)-lutein, (3R,3'R,6'S)-lutein, (3S,3'S,6'S)-lutein, (3S, 3'R,6'R)-lutein, (3S,3'R,6'S)-lutein or (3S,3'S,6'R)-lutein, or a combination thereof. In some embodiments, the compound of Formula (III) is (3R)-3-hydroxy-(β-ionylideneethyl)triphenylphosphonium salt or (3S)-3-hydroxy-(β-ionylideneethyl)triphenylphosphonium salt. In some embodiments, the triphenylphosphonium salt is a fluoride, chloride, bromide or iodide salt.

In one embodiment, the compound having the Formula II is prepared by deprotecting a compound having the Formula (IV):

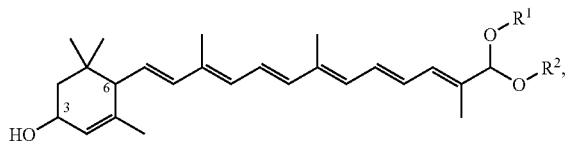

to obtain the compound having the Formula II, wherein $R^1$ and $R^2$ are independently a branched $C_1$-$C_7$ alkyl, a straight chain $C_1$-$C_7$ alkyl, or taken together form a 5-7 membered ring. In some embodiments, $R^1$ and $R^2$ are independently $C_1$-$C_7$ alkyl. In some embodiments, $R^1$ and $R^2$ are methyl. In some embodiments, the compound having the Formula (IV) is deprotected under mild acidic conditions without loss of optical purity. In some embodiments, the compound having the Formula (II) is (3R,6R)-3-hydroxy-12'-apo-ε-caroten-12'-al (6), (3S,6S)-3-hydroxy-12'-apo-ε-caroten-12'-al (7), (3S,6R)-3-hydroxy-12'-apo-ε-caroten-12'-al (8) or (3R,6S)-3-hydroxy-12'-apo-ε-caroten-12'-al (9), or a combination thereof. In some embodiments:

(i) (3R,6R)-3-hydroxy-12'-apo-ε-caroten-12'-al dimethylacetal (10) is deprotected to form (3R,6R)-3-hydroxy-12'-apo-ε-caroten-12'-al (6), (ii) (3S,6S)-3-hydroxy-12'-apo-ε-caroten-12'-al dimethylacetal (11) is deprotected to form 3S,6S)-3-hydroxy-12'-apo-ε-caroten-12'-al (7);

(iii) (3S,6R)-3-hydroxy-12'-apo-ε-caroten-12'-al dimethyl acetal (12) is deprotected to form (3S,6R)-3-hydroxy-12'-apo-ε-caroten-12'-al (8) or (iv) (3R,6S)-3-hydroxy-12'-apo-ε-caroten-12'-al dimethylacetal (13) is deprotected to form (3R,6S)-3-hydroxy-12'-apo-ε-caroten-12'-al (9).

In one embodiment, a compound having the Formula (IV) is prepared by elongating a compound having the Formula V:

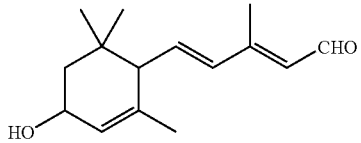

with a compound having the Formula VI:

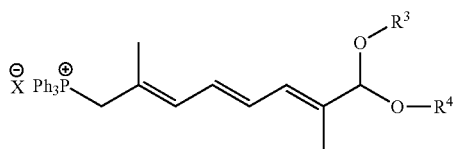

via Wittig coupling to obtain the compound having the Formula IV, where $X^\ominus$ is an anionic counterion such as Cl$^-$, Br$^-$ or I$^-$, wherein $R^3$ and $R^4$ are independently a branched $C_1$-$C_7$ alkyl, a straight chain $C_1$-$C_7$ alkyl, or taken together form a 5-7 membered ring. In some embodiments, $R^1$ and $R^2$ are independently $C_1$-$C_7$ alkyl. In some embodiments, $R^1$ and $R^2$ are methyl. In some embodiments, the compound having the Formula (IV) is protected $C_{25}$-hydroxyaldehyde 10, 11, 12, or 13, or a combination thereof. In some embodiments, the compound having the Formula (VI) is (all-E)-(7-formyl-2-methyl-2,4,6-octatrienyl)triphenylphosphonium salt. In some embodiments, the triphenylphosphonium salt is a chloride, bromide or iodide salt. In another embodiment:

(i) (all-E)-(7-formyl-2-methyl-2,4,6-octatrienyl)triphenylphosphonium salt is reacted with (7E,9E,3R,6R)-3-hydroxy-α-ionylideneacetaldehyde (15) to obtain protected $C_{25}$-hydroxyaldehyde 10;

(ii) (all-E)-(7-formyl-2-methyl-2,4,6-octatrienyl)triphenylphosphonium salt is reacted with (7E,9E,3S,6S)-3-hydroxy-α-ionylideneacetaldehyde (16) to obtain protected $C_{25}$-hydroxyaldehyde 11;

(iii) (all-E)-(7-formyl-2-methyl-2,4,6-octatrienyl)triphenylphosphonium salt is reacted with (7E,9E,3S,6R)-3-hydroxy-α-ionylideneacetaldehyde (17) to obtain protected $C_{25}$-hydroxyaldehyde 12; or (iv) (all-E)-(7-formyl-2-methyl-2,4,6-octatrienyl)triphenylphosphonium salt is reacted with (7E,9E,3R,6S)-3-hydroxy-α-ionylideneacetaldehyde (18) to obtain protected $C_{25}$-hydroxyaldehyde 13.

In one embodiment, the compound having the Formula V:

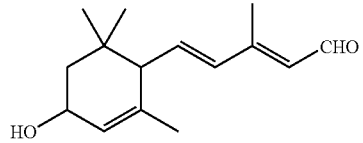

is prepared by reacting the cyano group of a compound having the Formula VII:

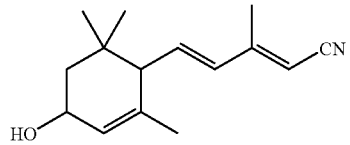

with a reducing agent to obtain the compound having the Formula V. In some embodiments, the compound having the Formula (V) is $C_{15}$-hydroxyaldehyde 15, 16, 17 and 18, or a combination thereof. In some embodiments, the compound having the Formula (VII) is (3R,6R)-3-hydroxy-α-ionylideneacetonitrile (19), (3S,6S)-3-hydroxy-α-ionylideneacetonitrile (20), (3S,6R)-3-hydroxy-α-ionylideneacetonitrile (21) or (3R,6S)-3-hydroxy-α-ionylideneacetonitrile (22), or a combination thereof.

In one embodiment, a mixture of $C_{15}$-hydroxynitriles (3R, 6R)-3-hydroxy-α-ionylideneacetonitrile (19), (3S,6S)-3-hydroxy-α-ionylideneacetonitrile (20), (3S,6R)-3-hydroxy-α-ionylideneacetonitrile (21) and (3R,6S)-3-hydroxy-α-ionylideneacetonitrile (22) is reduced with diisobutylaluminum hydride (DIBAL-H), to obtain a mixture of $C_{15}$-hydroxyaldehydes 15, 16, 17 and 18.

In some embodiments, a mixture of $C_{15}$-hydroxyaldehydes 15, 16, 17 and 18 is separated by using a combination of column chromatography and enzyme-mediated acylation. In some embodiments, a mixture of $C_{15}$-hydroxyaldehydes 15 and 16 is separated from the mixture of $C_{15}$-hydroxyaldehyde 15, 16, 17 and 18 by column chromatography using a combination of a hydrocarbon solvent selected from the group consisting of pentane, hexane, heptane and cyclohexane, and ethyl acetate or acetone, to obtain a mixture of $C_{15}$-hydroxyaldehydes 15 and 16. In some embodiments, the column chromatography is carried out on n-silica.

In some embodiments, the mixture of $C_{15}$-hydroxyaldehydes 15 and 16 is acylated with lipase AK (*Pseudomonas fluorescens*) or lipase PS (*Pseudomonas cepacia*) in the presence of an acyl donor such as vinyl acetate, wherein $C_{15}$-hydroxyaldehyde 16 is converted to (3S,6S)-3-acetoxy-α-ionylideneacetaldehyde (25) while $C_{15}$-hydroxyaldehyde 15 remains unesterified. In some embodiments, $C_{15}$-acetoxyaldehyde 25 is saponified with alcoholic potassium hydroxide (KOH) or sodium hydroxide (NaOH) to obtain $C_{15}$-hydroxyaldehyde 16.

In some embodiments, a mixture of $C_{15}$-hydroxyaldehydes 17 and 18 is separated from the mixture of $C_{15}$-hydroxyaldehyde 15, 16, 17 and 18 by column chromatography using a combination of a hydrocarbon solvent selected from the group consisting of pentane, hexane, heptane and cyclohexane, and ethyl acetate or acetone, to obtain a mixture of $C_{15}$-hydroxyaldehydes 17 and 18. In some embodiments, the column chromatography is carried out on n-silica. In some embodiments, the mixture of $C_{15}$-hydroxyaldehydes 17 and 18 is acylated with lipase AK (*Pseudomonas fluorescens*) or lipase PS (*Pseudomonas cepacia*) in the presence of an acyl donor such as vinyl acetate, wherein $C_{15}$-hydroxyaldehyde 17 is converted to (3S,6R)-3-acetoxy-α-ionylideneacetaldehyde (26) while $C_{15}$-hydroxyaldehyde 18 remains unesterified. In some embodiments, $C_{15}$-acetoxyaldehyde 26 is saponified with alcoholic potassium hydroxide (KOH) or sodium hydroxide (NaOH) to obtain $C_{15}$-hydroxyaldehyde 17.

In one embodiment, the ketone group of a compound having the Formula (VIII):

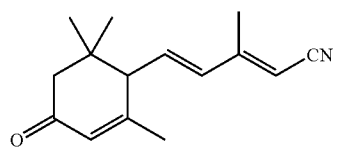

is reacted with a reducing agent, to obtain the compound having the Formula (VII):

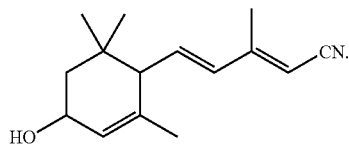

In some embodiments, the reducing agent is stereoselective. In some embodiments, a compound having the Formula (VIII) is (7E,9E)-3-keto-α-ionylideneacetonitrile (23a) or (7E,9Z)-3-keto-α-ionylideneacetonitrile (23b), or a combination thereof. In some embodiments, the compound having the Formula (VII) is (3R,6R)-3-hydroxy-α-ionylideneacetonitrile (19), (3S,6S)-3-hydroxy-α-ionylideneacetonitrile (20), (3S,6R)-3-hydroxy-α-ionylideneacetonitrile (21) or (3R,6S)-3-hydroxy-α-ionylideneacetonitrile (22), or a combination thereof.

In some embodiments, (7E,9E)-3-keto-α-ionylideneacetonitrile (23a) is stereoselectively reduced with a reducing agent to obtain (3,6-trans)-$C_{15}$-hydroxynitriles 19+20 and (3,6-cis)-$C_{15}$-hydroxynitriles 21+22 in a ratio ranging from 6:1 to 1:6. In some embodiments, the reducing agent is $NaBH_4$, $NaBH_4$/dl-tartaric acid, $NaBH_4$/d-tartaric acid, $NaBH_4$/l-tartaric acid, $NaBH_4$/dibenzoyl-d-tartaric acid, $NaAlH_2(OCH_2CH_2OMe)_2$ (RED-AL™), LiB[CHMeCH$_2$CH$_3$]$_3$H (L-SELECTRIDE™), NaB[CHMeCH$_2$CH$_3$]$_3$H (N-SELECTRIDE™), KB[CHMeCH$_2$CH$_3$]$_3$H (K-SELECTRIDE™), KB[CHMeCHMe$_2$]$_3$H (KS-SELECTRIDE™), $BH_3$/(R)-2-methyl-CBS-oxazaborolidine, or $BH_3$/(S)-2-methyl-CBS-oxazaborolidine.

In some embodiments, ketonitrile 23a is selectively reduced with KB[CHMeCH$_2$CH$_3$]$_3$H (K-SELECTRIDE™) to obtain (3,6-trans)-$C_{15}$-hydroxynitriles 19+20 as the major products and (3,6-cis)-$C_{15}$-hydroxynitriles 21+22 as the minor products.

In some embodiments, ketonitrile 23a is selectively reduced with $BH_3$/(R)-2-methyl-CBS-oxazaborolidine to obtain (3,6-cis)-$C_{15}$-hydroxynitriles 21+22 as the major products and (3,6-trans)-$C_{15}$-hydroxynitriles 19+20 as the minor products. In some embodiments, ketonitrile 23a is reduced to obtain a mixture of $C_{15}$-hydroxyaldehydes 15, 16, 17 and 18 by (i) reducing (7E,9E)-3-keto-α-ionylideneacetonitrile (23a) with a metal hydride reagent to form a mixture of $C_{15}$-hydroxynitriles 19, 20, 21 and 22 and (ii) reducing the mixture of $C_{15}$-hydroxynitriles 19, 20, 21 and 22 with DIBAL-H to obtain a mixture of $C_{15}$-hydroxyaldehydes 15, 16, 17 and 18 in a one-pot reaction. In some embodiments, the metal hydride reagent is $NaAlH_2(OCH_2CH_2OMe)_2$ (RED-AL™) LiB[CHMeCH$_2$CH$_3$]$_3$H (L-SELECTRIDE™), NaB[CHMeCH$_2$CH$_3$]$_3$H (N-SELECTRIDE™), KB[CHMeCH$_2$CH$_3$]$_3$H (K-SELECTRIDE™) or KB[CHMeCHMe$_2$]$_3$H (KS-SELECTRIDE™).

In one embodiment, a compound having the Formula (VIII):

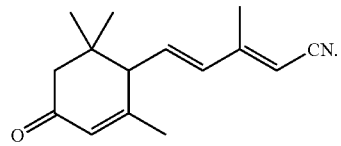

is prepared by reacting a compound having the Formula (IX):

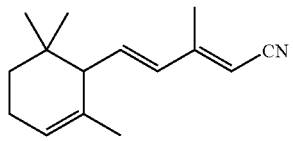

with an oxidizing agent, to obtain the compound having the Formula (VIII) via allylic oxidation. In some embodiments, the compound having the Formula (IX) is (7E,9E)-α-ionylideneacetonitrile (24a) or (7E,9Z)-α-ionylideneacetonitrile (24b), or a mixture thereof. In some embodiments, the compound having the Formula (VIII) is (7E,9E)-3-keto-α-ionylideneacetonitrile (23a) or (7E,9Z)-3-keto-α-ionylideneacetonitrile (23b), or a combination thereof.

In some embodiments, a mixture of (7E,9E)-α-ionylideneacetonitrile (24a) and (7E,9Z)-α-ionylideneacetonitrile (24b) in an isomeric ratio ranging from 3:1 to 12:1 is reacted with an oxidizing reagent, to obtain a mixture of (7E,9E)-3-keto-α-ionylideneacetonitrile (23a) and (7E,9Z)-3-keto-α-ionylideneacetonitrile (23b) in an isomeric ratio ranging from 3:1 to 12:1.

In some embodiments, a mixture of (7E,9E)-3-keto-α-ionylideneacetonitrile (23a) and (7E,9Z)-3-keto-α-ionylideneacetonitrile (23b) is purified by separating a mixture of ketonitrile 23a and ketonitrile 23b via crystallization with an alcohol such as ethanol, at a temperature ranging from −15 to 0° C.

In some embodiments, the compound having the Formula (IX) is a mixture of (7E,9E)-α-ionylideneacetonitrile (24a) and (7E,9Z)-α-ionylideneacetonitrile (24b) in an isomeric ratio ranging from 3:1 to 12:1 is oxidized with a combination of tert-BuOOH (TBHP) and bleach (5.25% NaOCl), at a temperature ranging from −5 to 0° C., in a solvent selected from the group consisting of acetonitrile (CH₃CN), methylene chloride (CH₂Cl₂), ethyl acetate, hexane, tetrahydrofuran (THF), tert-butyl methyl ether (TBME), dimethylformamide (DMF), dimethylsulfoxide (DMSO), ethylene glycol, a straight chain $C_1$-$C_5$ alcohol and a branched $C_1$-$C_5$ alcohol, to obtain the compound having the Formula (VIII) as a mixture of (7E,9E)-3-keto-α-ionylideneacetonitrile (23a) and (7E,9Z)-3-keto-α-ionylideneacetonitrile (23b).

In some embodiments, the compound having the Formula (IX) is a mixture of (7E,9E)-α-ionylideneacetonitrile (24a) and (7E,9Z)-α-ionylideneacetonitrile (24b) in an isomeric ratio ranging from 3:1 to 12:1 and is oxidized with a combination of tert-BuOOH (TBHP) and Pd/C at a temperature ranging from 0° C. to room temperature (R.T.), in a solvent selected from the group consisting of acetonitrile (CH₃CN), methylene chloride (CH₂Cl₂), ethyl acetate, hexane, tetrahydrofuran (THF), tert-butyl methyl ether (TBME), dimethylformamide (DMF), dimethylsulfoxide (DMSO), ethylene glycol, a straight chain $C_1$-$C_5$ alcohol and a branched $C_1$-$C_5$ alcohol, to obtain the compound having the Formula (VIII) as a mixture of (7E,9E)-3-keto-α-ionylideneacetonitrile (23a) and (7E,9Z)-3-keto-α-ionylideneacetonitrile (23b).

In some embodiments, a compound having the Formula (IX):

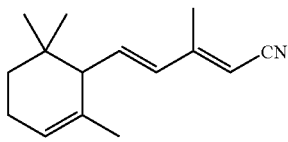

by condensing a compound having the Formula (X):

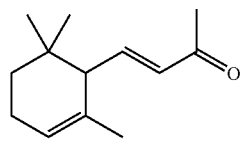

with cyanoacetic acid to obtain the compound having the Formula (IX). In some embodiments, the compound having the Formula (IX) is (7E,9E)-α-ionylideneacetonitrile (24a) or (7E,9Z)-α-ionylideneacetonitrile (24b), or a combination thereof. In some embodiments, the compound having the Formula (X) is (rac)-α-ionone.

In one embodiment, (rac)-α-ionone is condensed with cyanoacetic acid in the presence of an amine such as cyclohexylamine, at a temperature ranging from 80° C. to 100° C., to obtain (7E,9E)-α-ionylidene-acetonitrile (24a) and (7E,9Z)-α-ionylideneacetonitrile (24b) in a ratio of 12:1 or greater. In some embodiments, the mixture of nitriles 24a and 24b in an isomeric ratio of 12:1 or greater is purified by vacuum distillation, wherein the isomeric ratio of 24a and 24b is unaltered.

In one embodiment, (rac)-3-keto-α-ionone is prepared by reacting (rac)-α-ionone with an oxidizing agent to obtain (rac)-3-keto-α-ionone.

In some embodiments, (rac)-α-ionone is reacted with a combination of tert-BuOOH (TBHP) and bleach, at a temperature ranging from −5 to 0° C., in a solvent selected from the group consisting of acetonitrile (CH₃CN), methylene chloride (CH₂Cl₂), ethyl acetate, hexane, tetrahydrofuran (THF), tert-butyl methyl ether (TBME), dimethylformamide (DMF), dimethylsulfoxide (DMSO), ethylene glycol, a straight chain $C_1$-$C_5$ alcohol and a branched $C_1$-$C_5$ alcohol, to obtain to (rac)-3-keto-α-ionone.

In some embodiments, (rac)-α-ionone is reacted with a combination of tert-BuOOH (TBHP) and Pd/C, at a temperature ranging from 0° C. to room temperature (R.T.), in a solvent selected from the group consisting of acetonitrile (CH₃CN), methylene chloride (CH₂Cl₂), ethyl acetate, hexane, tetrahydrofuran (THF), tert-butyl methyl ether (TBME), dimethylformamide (DMF), dimethylsulfoxide (DMSO), ethylene glycol, a straight chain $C_1$-$C_5$ alcohol and a branched $C_1$-$C_5$ alcohol, to obtain to (rac)-3-keto-α-ionone. In some embodiments, ketonitriles 23a and 23b are prepared by condensing (rac)-3-keto-α-ionone with (EtO)₂P(O)CH₂CN or (iso-PrO)₂P(O)CH₂CN in the presence of a base to obtain ketonitriles 23a and 23b.

In one embodiment, a compound of the Formula XII is prepared by oxidatively degrading a compound having the Formula XI:

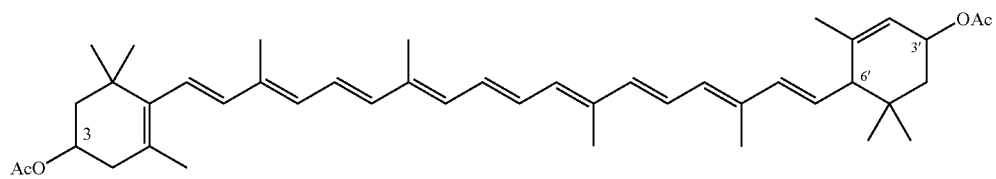

with an oxidizing agent, to obtain a compound of the Formula XII:

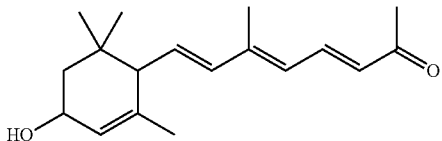

and a compound of the Formula XIII:

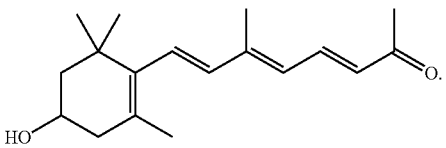

In some embodiments, the compound having the Formula (XI) is (3R,3'R,6'R)-lutein diacetate, (3R,3'S,6'S)-lutein diacetate, (3R,3'S, 6'R)-lutein diacetate, (3R,3'R,6'S)-lutein diacetate, (3S,3'S,6'S)-lutein diacetate, (3S,3'R,6'R)-lutein diacetate, (3S,3'R,6'S)-lutein diacetate or (3S,3'S,6'R)-lutein diacetate or a combination thereof.

In some embodiments, (3R,6R)-3-hydroxy-13-apo-ε-caroten-13-one (27) and (3R)-3-hydroxy-13-apo-β-caroten-13-one (28) are prepared by oxidatively degrading (3R,3'R, 6'R)-lutein diacetate with tert-BuOOH (TBHP) and bleach, at a temperature ranging from −5° C. to room temperature (R.T.), in a solvent selected from the group consisting of acetonitrile ($CH_3CN$), methylene chloride ($CH_2Cl_2$), ethyl acetate, hexane, tetrahydrofuran (THF), tent-butyl methyl ether (TBME), dimethylformamide (DMF), dimethylsulfoxide (DMSO), a straight chain $C_1$-$C_5$ alcohol and a branched $C_1$-$C_5$ alcohol to obtain (3R,6R)-3-hydroxy-13-apo-ε-caroten-13-one (27) and (3R)-3-hydroxy-13-apo-β-caroten-13-one (28).

BRIEF DESCRIPTION OF THE DRAWINGS/FIGURES

DETAILED DESCRIPTION OF THE INVENTION

All chemicals and reagents were commercially available and obtained from Aldrich Chemical Co. (St. Louis, Mo.). Lipase AK (*pseudomonas fluorescens*) and Lipase PS (*Pseudomonas cepacia*) were from Amano Enzyme USA (Lombard, Ill.). All carotenoids and their precursors were fully characterized by $^1H$ and $^{13}C$-NMR, MS, and UV-Vis, and circular dichroism (CD). Combination of NMR and CD was employed to assign the relative and absolute stereochemistry of all synthetic carotenoids and their precursors. The purity of all compounds was determined by HPLC on a silica-based nitrile bonded column (hexane, 75%; $CH_2Cl_2$ 25%; MeOH, 0.5%; 0.7 mL/min) and a chiral HPLC [amylose tris-(3,5-dimethylphenylcarbamate)] column was employed to assess the optical purity of stereoisomers. The absolute configurations of $C_{15}$-hydroxynitriles 19-22 and $C_{15}$-hydroxyaldehydes 15-18 were unequivocally established by comparison of their NMR and CD spectra with those of (3R,6R)-3-hydroxy-13-apo-ε-caroten-13-one which was prepared from oxidative degradation of naturally occurring (3R,3'R,6'R)-lutein.

Figure 1:
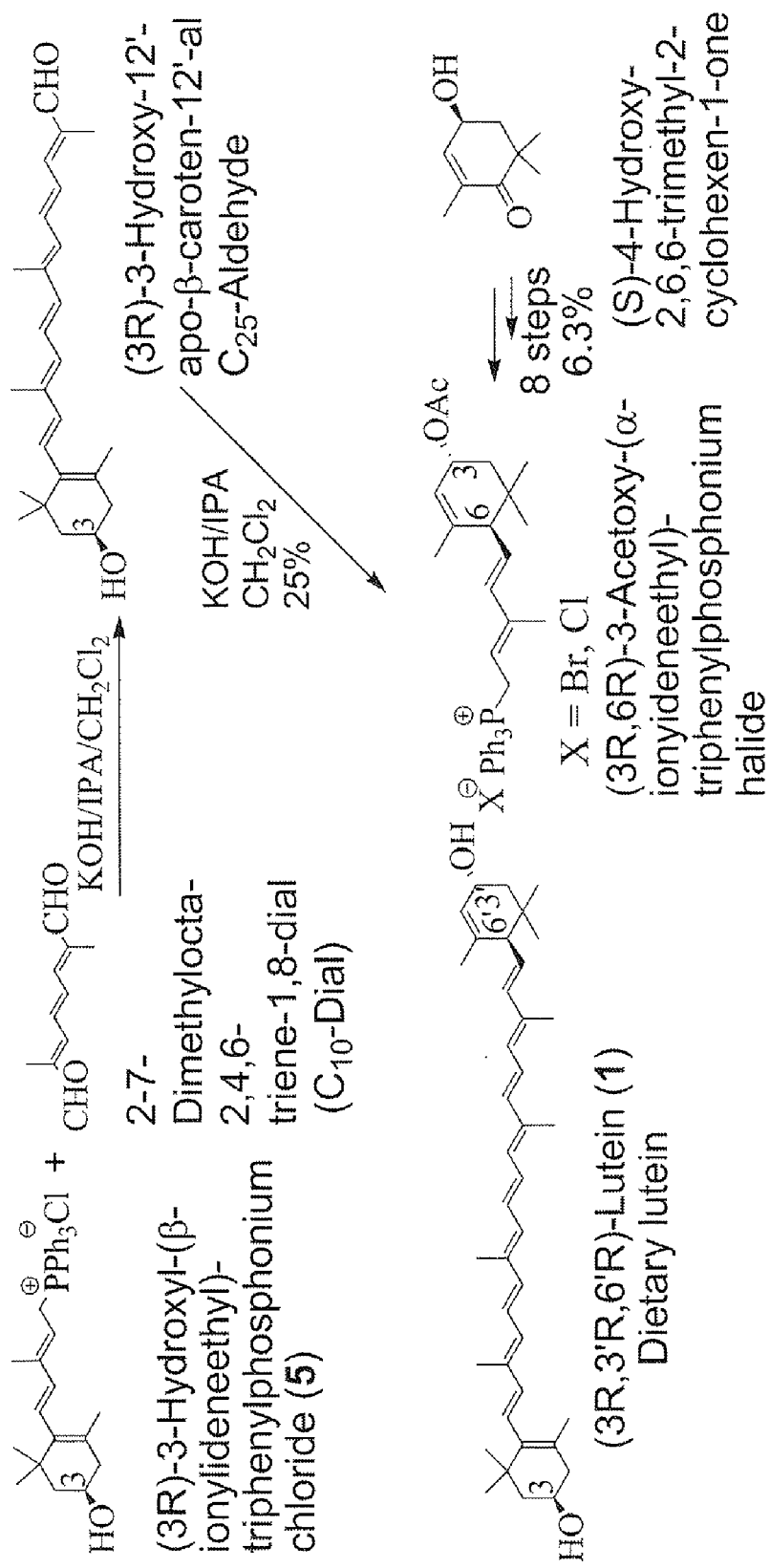
FIG. 1 is a schematic representation of the total synthesis of dietary (3R,3'R,6'R)-lutein according to the published procedure by Mayer and Ruttimann (*Helv. Chim Acta*, 1980, vol. 63, pp. 1451-1455).
Figure 2:
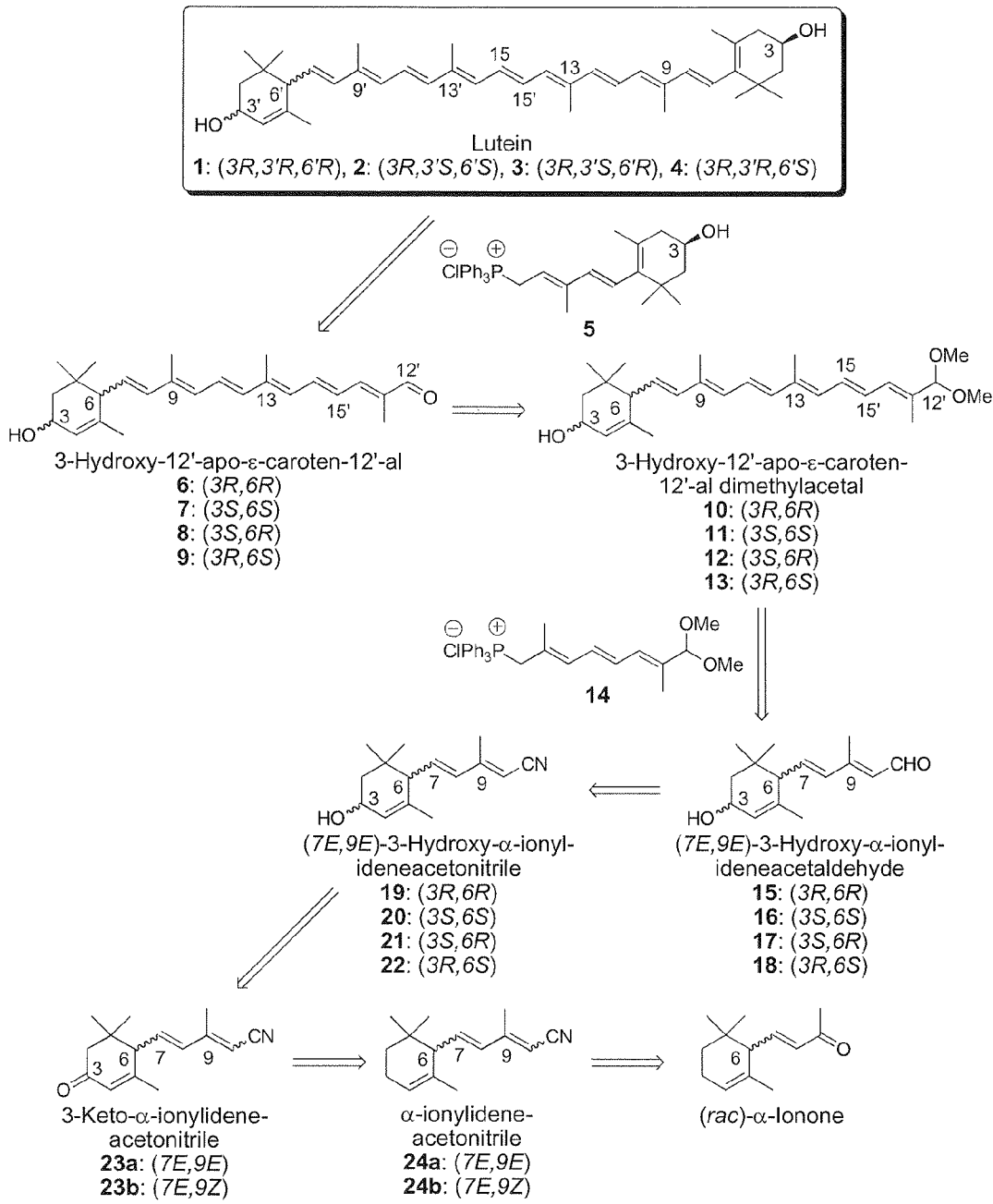
FIG. 2 is a schematic representation of the retrosynthesis of four stereoisomers of lutein from (rac)-α-ionone (the cartenoid numbering system has been used for all end-group precursors of luteins).
Figure 3:
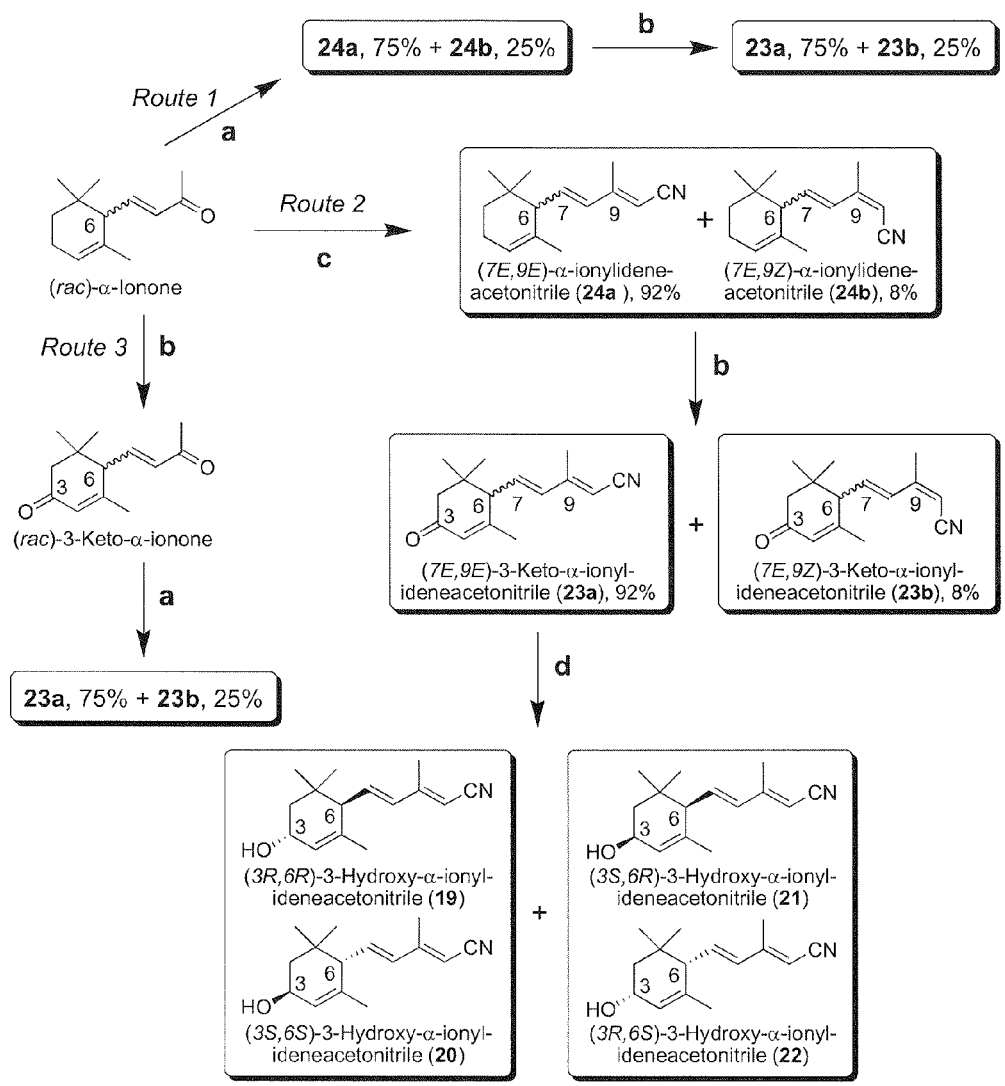
FIG. 3 is a schematic representation of the synthesis of (7E,9E)-3-hydroxy-α-ionylideneacetonitriles 19-22 from (rac)-α-ionone (the cartenoid numbering system has been used for all end-group precursors of luteins).

Synthesis of (7E,9E)-3-Keto-α-ionylideneacetonitrile (23a) from (rac)-α-Ionone. In one embodiment of the present invention, HWE reaction of commercially available (rac)-α-ionone with diethyl cyanomethylphosphonate in dry tert-butyl methyl ether (TBME) or tetrahydrofuran (THF) using NaH or NaOMe/MeOH as base gave (7E,9E)-nitrile 24a (75%) and (7E,9Z)-nitrile 24b (25%) in 74% isolated yield after distillation (Route 1, FIG. 3). Alternatively, diisopropyl cyanomethylphosphonate could also be used with similar results. A mixture of nitriles 24a and 24b was then oxidized with tert-BuOOH (TBHP, 70% in water), household bleach, and catalytic amounts of $K_2CO_3$ in acetonitrile at −5 to 0° C. to yield ketonitriles 23a (75%) and 23b (25%). After purification by chromatography, a mixture of these nitriles was obtained in 57% yield. This mixture was crystallized from ethanol at −15° C. to give the (7E,9E)-ketonitrile 23a as a white crystal free from 23b in 37% isolated yield. While this reaction can be carried out in other solvents such as ethyl acetate, ethylene glycol, and hexane, the highest isolated yield of 57% was obtained with acetonitrile and ethanol. This water-based oxidation system, using household laundry bleach and aqueous TBHP, has been shown to convert steroidal olefins to α,β-enones by an economical and environmentally friendly methodology (Marwah, *Green Chem.*, 2004, 6, 570-577). Ketonitriles 23a and 23b were also prepared in 53% yield by palladium(II)-mediated oxidation of nitriles 24a and 24b with TBHP in dichloromethane ($CH_2Cl_2$) at 0° C. similar to a methodology that has been employed for allylic oxidation of olefins (Yu and Corey, *Org. Lett.* 2002, 4: 2727-2730). However to date, there are no literature reports on the direct oxidation of nitriles 24a and 24b to ketonitriles 23a and 23b. These oxidation reactions clearly revealed that conversion of a mixture of 24a/24b to 23a/23b is not accompanied by E/Z-isomerization and the isomeric ratio of these nitriles remains unchanged. As mentioned earlier, the reduction of a mixture of ketonitriles 23a and 23b can yield a complicated mixture of (7E,9E)- and (7E,9Z)-hydroxynitriles 19-22 that would be difficult to separate in high optical purity (FIG. 3). Therefore, an alternative process was needed that could preferably provide 23a or its precursor 24a as a single isomer. It has been previously shown that Knoevenagel condensation of 13-ionone with cyanoacetic acid in boiling pyridine (115° C.) in the presence of catalytic amounts of piperidinium acetate affords 13-ionylideneacetonitrile in 75% yield, predominantly as the (7E,9E)-isomer (Andriamialisoa et al. *Tetrahedron Lett.*, 1993, 34: 8091-8092). However, in this literature report, the isomeric ratio of (7E,9E)/(7E,9Z) was not specified. When we applied the reported reaction conditions employed with β-ionone to condensation of (rac)-α-ionone with cyanoacetic acid, no reaction was observed. After examining this reaction with a number of organic amines, we discovered that cyclohexylamine could promote this reaction under mild conditions to give a high yield of (7E,9E)-α-ionylideneacetonitrile (24a) (Route 2, FIG. 3).

Therefore, in a preferred embodiment, Knoevenagel condensation of (rac)-α-ionone (1 eq) with cyanoacetic acid (1.3 eq) in cyclohexylamine (3 eq), also used as solvent, at 80-85° C. after 3.5 h affords 24a (92%) and 24b (8%) as a colorless oil in 75% isolated yield after distillation. Another reported method for the synthesis of α-ionylideneacetonitrile and β-ionylideneacetonitrile, involves condensation of α-ionone or β-ionone with methyl cyanoacetate in the presence of glacial acetic acid, acetamide, and ammonium acetate to yield the corresponding methyl α-ionylidenecyanoacetate or methyl β-ionylidenecyanoacetate (Young et al. *J. Am. Chem. Soc.*, 1944, 66: 520-524). These esters were then saponified to their corresponding α- or β-ionylidenecyanoacetic acid and subsequently decarboxylated to α- or β-ionylideneacetonitrile. Due to the old nature of this publication and lack of sophisticated analytical methods in 1944, the ratio of (7E,9E)/(7E,9Z) isomers in these nitriles were not reported.

In the following step, the mixture of 24a:24b=92%:8% (1 eq) and $K_2CO_3$ (0.1 eq) in acetonitrile (16 eq) was oxidized with tert-BuOOH (TBHP, 70% in water, 7 eq) and household bleach containing 5.25% NaOCl (2 eq of NaOCl) at −5 to 0° C. under nitrogen to yield ketonitriles 23a (92%) and 23b (8%). After extraction with ethyl acetate (EtOAc), the product was then purified by column chromatography (n-Silica) employing hexane:EtOAc (90%:10 to 70%:30%) to give a mixture of 23a (92%) and 23b (8%) in 53% yield. When this mixture was dissolved in ethanol and cooled down to −15° C., (7E,9E)-ketonitrile 23a was obtained as white crystals in 37% isolated yield and contained no measurable amounts of 23b. Therefore the present invention relates to two novel routes that converts (rac)-α-ionone to a single isomer of (7E,9E)-3-keto-α-ionylideneacetonitrile (23a) in crystalline form via allylic oxidation of α-ionylideneacetonitriles 24a and 24b. Depending on the selected route, the isomeric (7E,9E):(7E,9Z) ratio of nitriles 24a:24b may vary from 75%:25% to 92%:8% (Routes 1 and 2, FIG. 3).

In an alternative embodiment (Route 3, FIG. 3), (rac)-α-ionone was oxidized to crystalline (rac)-3-keto-α-ionone with TBHP (70% in water), bleach, and catalytic amounts of $K_2CO_3$ in ethyl acetate at −5 to 0° C. in 64% isolated yield. The palladium(II)-mediated oxidation of (rac)-α-ionone with TBHP in $CH_2Cl_2$ also afforded this ketone as a white crystalline solid in 53% isolated yield. There are three reported procedures for preparation of (rac)-3-keto-α-ionone in the literature. The first procedure employs tert-butyl chromate to oxidize (rac)-α-ionone to (rac)-3-keto-α-ionone in only 14% isolated yield (Prelog and Osgan, *Helv. Chim. Acta*, 1952, 35: 986-992) and the second uses $Ac_2Co.4H_2O/NH_4Br/O_2$ to improve the yield to 31% (Widmer et al., *Helv. Chim. Acta* 1982, 65: 944-57). More recently, another procedure for allylic oxidation of ionone-like dienes with TBHP catalyzed by $CaCl_2$ and $MgCl_2.6H_2O$ at 60° C. has also been reported that can afford (rac)-3-keto-α-ionone in yields comparable to ours (Yang et al. Synlett 2006, 16: 2617-2620).

Figure 4:
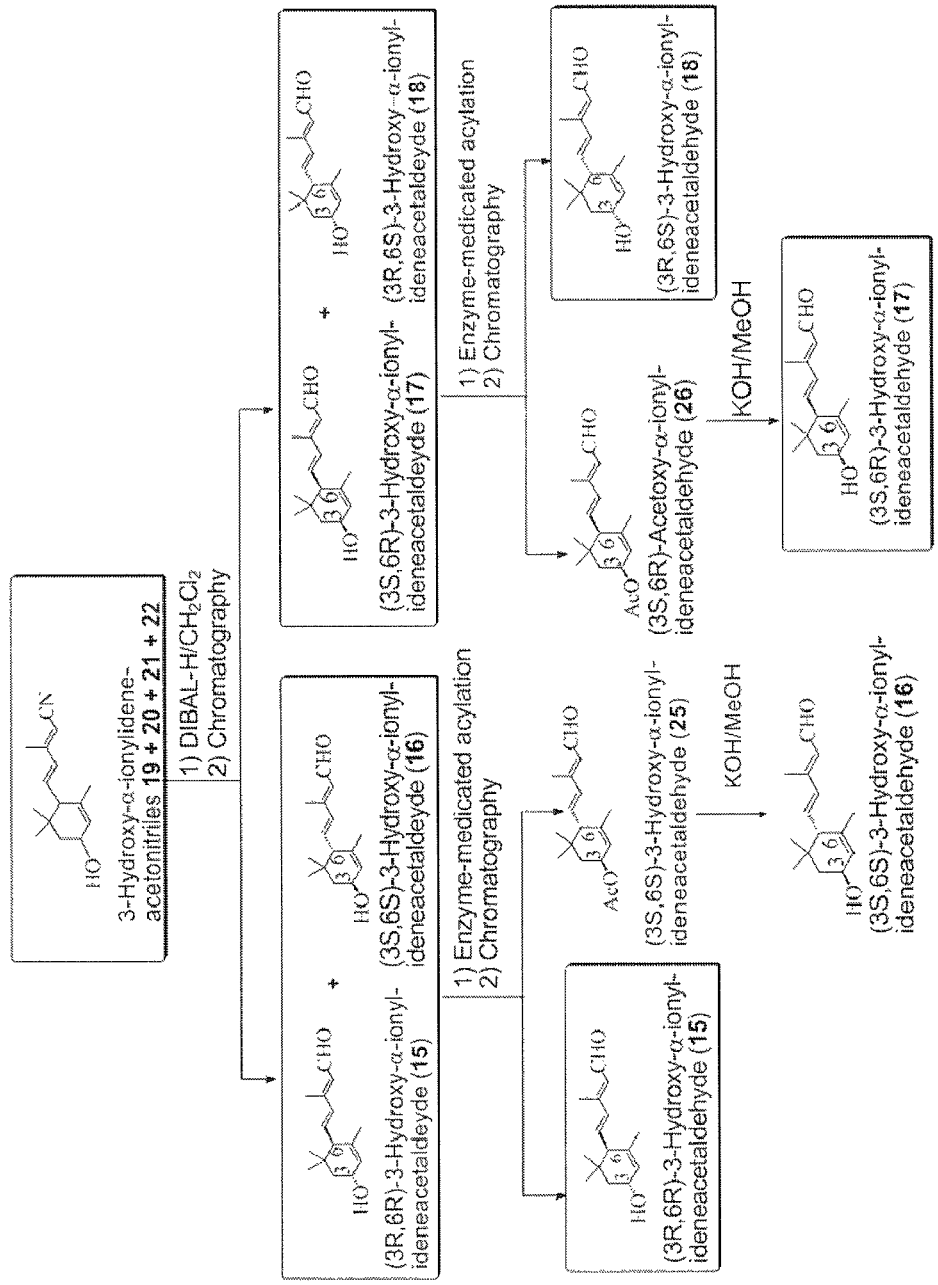
FIG. 4 is a schematic representation of the synthesis and separation of optically pure $C_{15}$-hydroxyaldehydes 15-18 employed as precursors for the total synthesis of stereoisomer luteins (the cartenoid numbering system has been used for all end-group precursors of lutein).

The HWE reaction of (rac)-3-keto-α-ionone with diethyl cyanomethylphosphonate in TBME or THF gave (rac)-ketonitrile 23a (75%) and 23b (25%) in 81% yield. After purification by flash chromatography and crystallization from ethanol at −15° C., (7E,9E)-ketonitrile 23a was obtained as white crystals in 40% isolated yield. This reaction has been previously reported by Imai et al. to yield a mixture of 23a and 23b as an oil that was not crystallized and the isomeric ratio of these ketonitriles were not reported (Imai, *Photochem. Photobiol.* 1999, 70: 111-115). Our methodology for the synthesis of ketonitriles 23a and 23b according to the routes 1 and 2, as shown in FIG. 4, is novel and has not been reported previously. Further, the present invention, for the first time, describes the isolation of (7E,9E)-ketonitrile 23a as a single isomer by crystallization in greater than 98% purity with virtually no contamination from its (7E,9Z)-isomer (23b).

Reduction of (7E,9E)-3-keto-α-ionylideneacetonitrile (23a) to (7E,9E)-3-hydroxy-α-ionylideneacetonitriles 19-22. As shown in FIG. 3, (7E,9E)-ketonitrile 23a was reduced to four stereoisomeric hydroxynitriles 19-22 with a number of reagents in 92-97% yield and the results are shown in Table 1. Because (3R,6R)-hydroxynitrile 19 with a trans relationship between the OH at C3 and C6-dienenitrile side chain is the precursor of the naturally occurring (3R,3'R,6'R)-lutein (1), it was desirable to increase the composition of the trans-hydroxynitriles 19 and 20 relative to the cis-hydroxynitriles 21 and 22 in the reduction products. The reduction of ketonitrile 23a with $NaBH_4$ was very sluggish and showed no selectivity with respect to the relative stereochemistry at C3 and C6. This was determined by HPLC analysis of the products employing a silica-based nitrile bonded column that allowed the separation of trans-hydroxynitriles (19+20) from cis-hydroxynitriles (21+22). The reduction products were also monitored by chiral HPLC that allowed the separation of all four stereoisomers of hydroxynitriles 19-22. While the reduction with TIBA was quite efficient even at low temperature (−40° C.), the relative composition of trans-hydroxynitriles (19+20) to cis-hydroxynitriles (21+22) could not be dramatically affected. However, the reduction of ketonitrile 23a with a combination of $NaBH_4$ and dl-tartaric acid provided trans-hydroxynitriles (19+20) as the major products (75%) and the cis-hydroxynitriles (21+22) as the minor products (25%). The use of enantiomerically pure d- or l-tartaric acid or their 2,3-dibenzoyl derivatives did not improve the stereoselectivity of this reduction. There are only several reported examples of the use of the combination of $NaBH_4$ and tartaric acid and its derivatives in the reduction of ketones but none of these examples involve the reduction of cyclic α,β-enones (Hirao et al., *Agric. Biol. Chem.* 1981, 45: 693-697; Adams, *Synth. Commun.* 1984, 14: 955-959; Yatagai and Ohnuki, *J. Chem. Soc. Perkin Trans.* 1 1990, 1826-1828; Cordes et al., *Eur. J. Org. Chem.* 2005, 24: 5289-5295).

TABLE 1

Reduction of ketonitrile 23a to hydroxynitriles 19-22 with various reagents.

| Reducing agent | Solvent | Temperature (Time, h) | (19 + 20):((21 + 22) (trans:cis)* |
|---|---|---|---|
| NaBH$_4$ | EtOH:H$_2$O 1.4:1 | 0° C. to R.T. (24 h) | 1:1 |
| Triisobutylaluminum (TIBA) | Toluene | −40° C. to R.T. (1 h) | 2:3 |
| NaBH$_4$/dl-Tartaric acid (3/1) | EtOH | −10 to −15° C. (2 h) | 3:1 |
| NaBH$_4$/d-Tartaric acid (3/1) | EtOH | −10 to −15° C. (2 h) | 3:1 |
| NaBH$_4$/l-Tartaric acid (3/1) | EtOH | −10 to −15° C. (2 h) | 3:1 |
| NaBH$_4$/Dibenzoyl-d-tartaric acid (3/1) | EtOH | −10 to −15° C. (2 h) | 3:1 |
| Sodium bis(2-methoxyethoxy)-aluminum hydride, NaAlH$_2$(OCH$_2$CH$_2$OMe)$_2$ (RED-AL ™) | TBME | −5 to 0° C. (1 h) | 1.3:1 |
| Lithium tri-sec-butylborohydride, LiB[CHMeCH$_2$CH$_3$]$_3$H (L-SELECTRIDE ™) | TBME | −30° C. (0.5 h) | 1.2:1 |
| Sodium tri-sec-butylborohydride, NaB[CHMeCH$_2$CH$_3$]$_3$H (N-SELECTRIDE ™) | TBME | −30° C. (0.5 h) | 2.5:1 |
| Potassium tri-sec-butylborohydride KB[CHMeCH$_2$CH$_3$]$_3$H (K-SELECTRIDE ™) | TBME | −30° C. (0.5 h) | 6:1 |
| Potassium trisiamylborohydride, KB[CHMeCHMe$_2$]$_3$H (KS-SELECTRIDE ™) | TBME | −30 to 0° C. (2 h) | 2.2:1 |
| BH$_3$/(R)-2-methyl-CBS-oxazaborolidine | TBME | 0° C., (1.5 h) | 1:6 |
| BH$_3$/(S)-2-methyl-CBS-oxazaborolidine | TBME | 0° C., (1.5 h) | 1:3 |

*Indicates the stereochemical relationship between the hydroxyl group at C3 and the dienenitrile side chain at C6.

The reduction of 23a with sodium bis(2-methoxyethoxy) aluminum hydride (RED-AL™) or lithium tri-sec-butylborohydride (L-SELECTRIDE™) produced essentially the same results and did not show a significant preference for the formation of trans-hydroxynitriles (19+20). However, when sodium tri-sec-butylborohydride (N-SELECTRIDE™) or potassium tri-sec-butylborohydride (K-SELECTRIDE™) were employed as the reducing agents, the relative composition of trans-hydroxynitriles (19+20) to cis-hydroxynitriles (21+22) was 71%:29% and 84%:16%, respectively.

The reduction of 23a with potassium trisiamylborohydride (KS-SELECTRIDE™) did not improve the results obtained with K-SELECTRIDE™ and afforded the trans-hydroxynitriles (19+20, 69%) as the major products and cis-hydroxynitriles (21+22, 31%) as the minor products.

Contrary to the results obtained with K-SELECTRIDE™, the reduction of ketonitrile 23a with BH$_3$/(R)-2-methyl-CBS-oxazaborolidine gave cis-hydroxynitriles (21+22) as the major products (86%) and the trans-hydroxynitriles (19+20) as the minor products (14%). When BH$_3$/(S)-2-methyl-CBS-oxazaborolidine was used as the reducing agent, the cis-hydroxynitriles (21+22) were still obtained as the major products but the stereoselectivity was not as high as that obtained with the R-isomer of CBS-oxazaborolidine.

Therefore, the present invention relates to a stereoselective method for reducing ketonitrile 23a to hydroxynitriles 19-22 in which the ratio of trans-hydroxynitriles (19+20) to that of cis-hydroxynitriles (21+22) can be controlled by the use of appropriate reducing agents and can vary from 6:1 to 1:6.

Synthesis of optically pure hydroxyaldehydes 15-18 from hydroxynitriles 19-22. In one embodiment of the present invention, a mixture of the four hydroxynitriles 19-22 was reduced with DIBAL-H in dichloromethane to a racemic mixture of hydroxyaldehydes 15-18 in 95% yield. In the following step, a mixture of hydroxyaldehydes 15 and 16 was readily separated from a mixture of hydroxyaldehydes 17 and 18 by column chromatography (FIG. 4). The direct reduction of ketonitrile 23a to hydroxyaldehydes 15-18 could also be accomplished in a one-pot reaction using K-SELECTRIDE™ followed by reduction with DIBAL-H to yield 15+16 (86%) as the major products and 17+18 (14%) as the minor products.

The racemic mixture of hydroxyaldehydes 15 and 16 were separated by enzyme-mediated acylation with lipase AK (*Pseudomonas fluorescens*) in refluxing pentane in the presence of vinyl acetate within 48 h. While hydroxyaldehyde 16 was acylated to acetoxyaldehyde 25, hydroxyaldehyde 15 remained unreacted. Due to their large difference in their solubility properties, 25 and 15 were readily separated by column chromatography. Acetoxyaldehyde 25 was nearly quantitatively hydrolyzed to hydroxyaldehyde 16 with KOH/MeOH at 0° C. to prevent the degradation of this sensitive end-group. According to chiral HPLC, (3R,6R)-3-hydroxy-α-ionylideneacetaldehyde (15) and (3S,6S)-3-hydroxy-α-ionylideneacetaldehyde (16) were obtained in enantiomeric excess (ee) of 94% and 93%, respectively.

Employing this overall strategy, the racemic mixture of hydroxyaldehydes 17 and 18 were similarly resolved by enzyme-mediated acylation with immobilized lipase AK (*Pseudomonas fluorescens*) in refluxing pentane in the presence of vinyl acetate in 50 h. Hydroxyaldehyde 17 underwent acylation to acetoxyaldehyde 26 while hydroxyaldehyde 18 remained unreacted (FIG. 4). Separation of 18 and 26 was readily accomplished by column chromatography. This afforded (3R,6S)-3-hydroxy-α-ionylideneacetaldehyde (18) as a single enantiomer in an ee of 92%. Alkaline hydrolysis of 26 with KOH/MeOH at 0° C., provided (3S,6R)-3-hydroxy-α-ionylideneacetaldehyde (17) in an ee of 91%.

Figure 5:
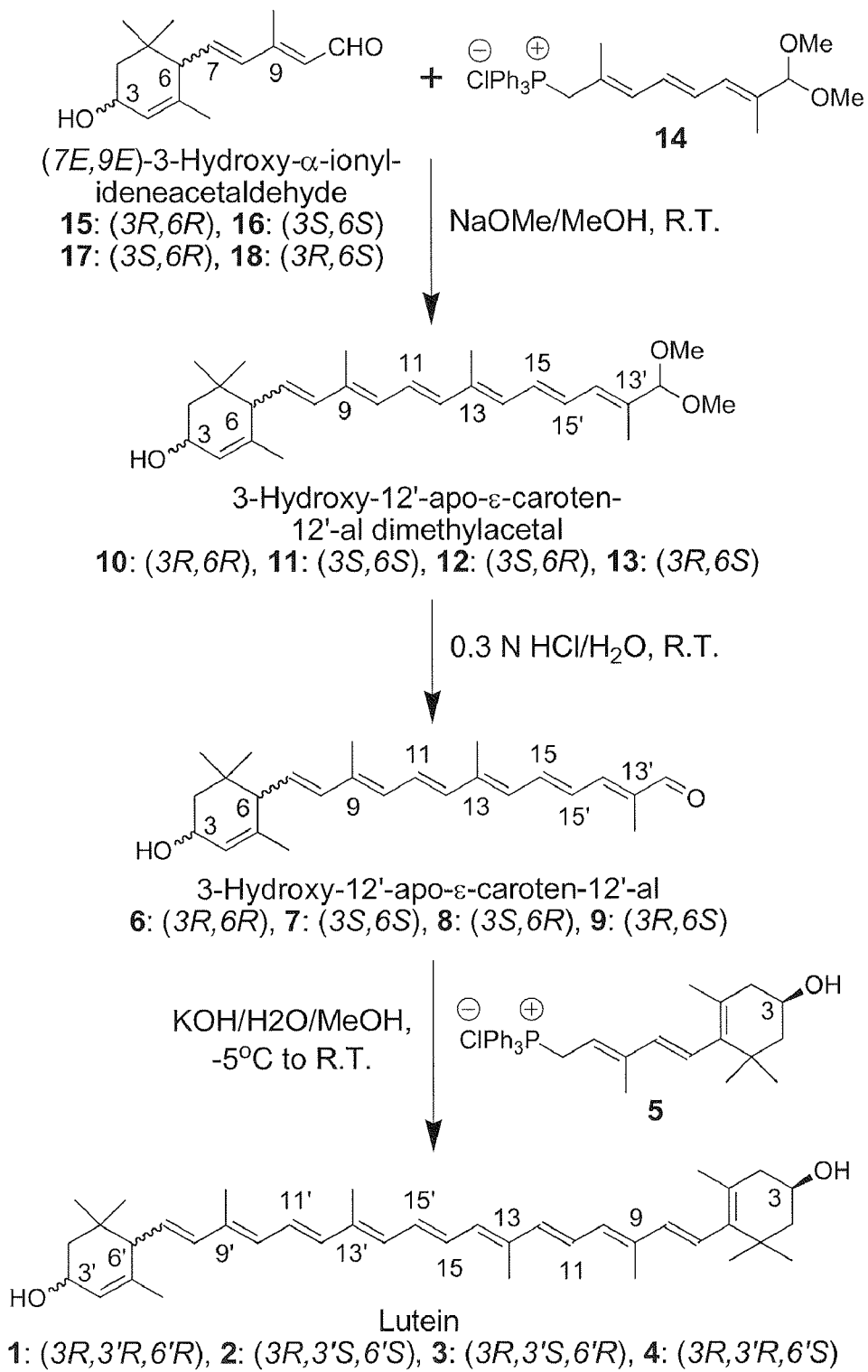
FIG. 5 is a schematic representation of the synthesis of lutein 1-4 from hydroxyaldehydes 15-18.

Therefore, all four hydroxyaldehydes 15-18 became accessible in optical purities ranging from 91-94%. These hydroxyaldehydes were subsequently used in the synthesis of the stereoisomeric luteins 1-4 via $C_{25}$-hydroxy-apocarotenals 6-9 as shown in FIG. 5.

Figure 6:
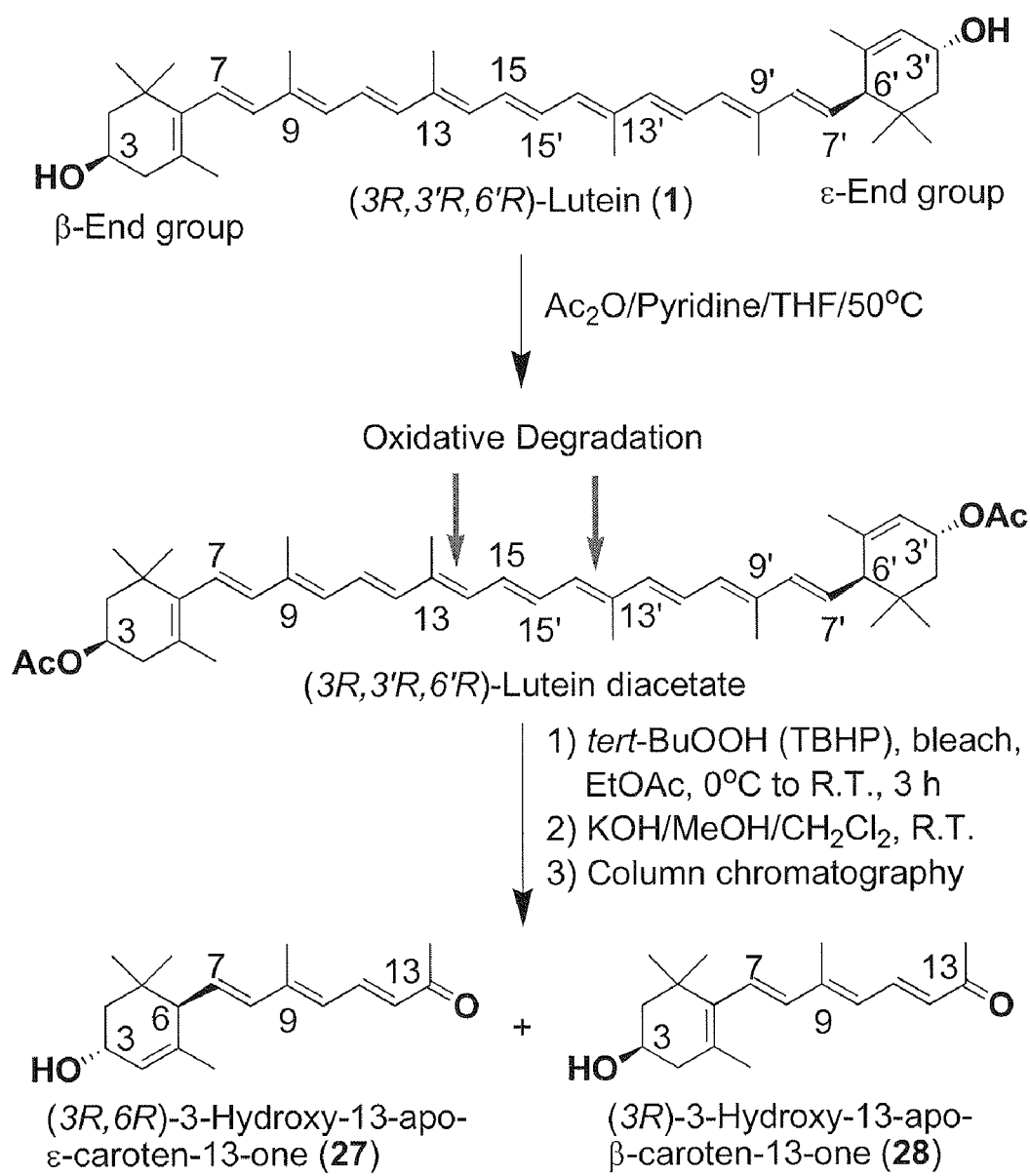
FIG. 6 is the schematic representation of the oxidative degradation of (3R,3'R,6'R)-lutein diacetate to $C_{18}$-ketones 27 and 28.

Determination of the absolute configuration of $C_{15}$-hydroxyaldehydes 15-18. In an attempt to determine the absolute configuration of the four $C_{15}$-hydroxyaldehydes 15-18, a model compound in which the stereochemistry at C3 and C6 is known was needed. Such a model compound could be prepared from oxidative cleavage of the polyene chain of naturally occurring (3R,3'R,6'R)-lutein in which the stereochemistry in the ε-end group of this carotenoid at C3' and C6' is known to be R. It has been well established that the oxidative cleavage (degradation) of carotenoids results in the formation of numerous ketones, aldehydes, and acids that are known as apocarotenones, apocarotenals, and apocarotenoic acids, respectively. Our overall strategy for the preparation of a model compound by oxidative degradation of (3R,3'R,6'R)-lutein is shown in FIG. 6. However, prior to oxidative cleavage of (3R,3'R,6'R)-lutein, the two hydroxyl groups in this carotenoid had to be protected. Therefore, (3R,3'R,6'R)-lutein was first acylated with acetic anhydride/Et₃N/TBME at 50° C. and the resulting (3R,3'R,6'R)-lutein diacetate was then subjected to oxidative degradation with TBHP/bleach. The reaction conditions for this oxidative degradation was similar to those used in oxidation of α-ionylideneacetonitrile (24a/24b) to 3-keto-α-ionylideneacetonitrile (23a/23b) described earlier. The only exception was that after the addition of bleach at 0° C., the reaction mixture was allowed to warm up to ambient temperature and stirred for 3 h to complete the oxidative cleavage of lutein diacetate (FIG. 6).

After alkaline hydrolysis (KOH/MeOH) followed by column chromatography, HPLC analysis of the partially purified product showed the presence of numerous oxidation products of lutein. Among these, (3R,6R)-3-hydroxy-13-apo-ε-caroten-13-one (27) with an ε-end group and (3R)-3-hydroxy-13-apo-β-caroten-13-one (28) with a β-end group were the major stable products. These were isolated by semipreparative HPLC and fully characterized from their NMR, MS, UV-Vis, and CD spectra. Comparison of the CD and NMR spectra of $C_{18}$-ketone 27 with those of the individually purified $C_{15}$-hydroxyaldehydes 15-18 established the absolute configuration of these compounds.

Synthesis of Luteins 1-4 via $C_{25}$-Hydroxy-Apocarotenals 6-9. The transformation of hydroxyaldehydes 15-18 to luteins 1-4 is shown in FIG. 5. In one embodiment of the present invention, the optically pure $C_{15}$-hydroxyaldehydes 15-18 were first elongated to their corresponding protected $C_{25}$-aldehydes 10-13 by olefination with the protected Wittig salt 14 in the presence of NaOMe/MeOH at ambient temperature. After solvent evaporation and without isolation of the products, the $C_{25}$-acetals 10-13 that were obtained as a mixture of all-E and 11Z were deprotected in dilute aqueous HCl (0.3 N) in acetone to give $C_{25}$-aldehydes 6-9 as a mixture of all-E and 11Z in isolated yields ranging from 75-85%. Under the conditions employed for the deprotection of acetals 10-13, the hydroxyl group at C3 did not undergo epimerization and the optical purities of the resulting $C_{25}$-aldehydes 6-9 were not compromised. This was confirmed by chiral HPLC of the individually synthesized $C_{25}$-aldehydes. The 11Z-isomers of $C_{25}$-aldehydes 6-9 could be catalytically isomerized to their corresponding all-E-isomers in the presence of palladium (II) acetate in refluxing ethyl acetate within 2 h. However, in a simplified process, this step was shown to be unnecessary and the isomerization of the 11Z and 11'Z-bonds that are formed by Wittig coupling reactions could be postponed until after luteins 1-4 were prepared.

As mentioned earlier, the preparation and application of the Wittig salt 14 in the total synthesis of carotenoids has been well documented in the literature but this building block has never been employed for the synthesis of lutein nor it has been applied to the synthesis of its precursors, the $C_{25}$-acetals 10-13 or $C_{25}$-hydroxyaldehydes 6-9.

In the final step of the synthesis of luteins, each of the $C_{25}$-hydroxyaldehydes 6-9 that were prepared as a mixture of all-E and 11Z-isomers were allowed to react with the Wittig salt 5 to yield their corresponding luteins 1-4 as a mixture of all-E and 11Z,11'Z-isomers. Each of the individually prepared E/Z-lutein was then thermally isomerized to its corresponding all-E isomer in a refluxing solution of ethyl acetate within 4 h. The isolated yields of all-E-luteins 1-4 in the final step of this synthesis ranged from 65-74%. The Wittig salt 5 was prepared according to published procedures (Widmer et al., *Helv. Chim. Acta*, 1990, 73: 861-867; Soukup et al., *Helv. Chim. Acta*, 1990, 73: 868-873). Similarly, the same strategy described above can also be used to elongate $C_{25}$-hydroxyaldehydes 6-9 with the S-enantiomer of Wittig salt 5 to synthesize the other four stereoisomers of luteins 1-4; these are: (3S,3'S,6'S)-lutein, (3S,3'R,6'R)-lutein, (3S,3'R,6'S)-lutein, and (3S,3'S,6'R)-lutein.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Synthesis of (rac)-α-Ionylideneacetonitrile (24a/24b) (Route 1, FIG. 3)

Methanol (70 mL) was transferred into a 500 mL three-necked flask equipped with a nitrogen inlet, a thermometer, and an addition funnel. The flask was cooled down in an ice bath under $N_2$ and sodium (5.47 g, 0.238 mol) washed with hexane, was added in small portions by maintaining the temperature below 10° C. After the sodium was completely dissolved, the solution was stirred at R.T. for 15 minutes and then cooled down to 0° C. A solution of diisopropyl cyanomethylphosphonate (47 g of 95% pure, 44.65 g, 0.218 mol) in TBME (20 mL) was added dropwise at 0-5° C. in 20 min. The ice bath was removed and the mixture was allowed to stir at R.T. for 1 h. The reaction mixture was cooled down in an ice bath and freshly distilled rac-α-ionone (38.10 g, 0.198 mol) in TBME (20 mL) was added dropwise in 45 min at 0-5° C. The mixture was allowed to warm up to room temperature and stirred for 4 h under $N_2$. The product was quenched with water (100 mL) and the organic layer was removed. The aqueous layer was extracted with TBME (2×50 mL) and the combined organic layer was sequentially washed with brine and water, dried over $Na_2SO_4$, and evaporated to dryness to give 45.4 g of a pale yellow oil. The crude product was purified by fractional distillation to yield a mixture of 24a and 24b (b.p.=107-

110° C. at 10 mm) as a colorless oil (31.6 g, 0.147 mol, 74%) which was shown by $^1$H- and $^{13}$C-NMR to consist of an isomeric mixture of 7E,9E:7E,9Z=3:1.

Example 2

Oxidation of (rac)-α-Ionylideneacetonitrile (24a/24b) to (rac)-3-Keto-α-Ionylideneacetonitrile (23a/23b) by Bleach and Aqueous TBHP (rac)-α-Ionylideneacetonitrile (13.15 g, 61.06 mmol) was transferred into a 500 mL three-necked flask using acetonitrile (30 mL, 23.58 g, 0.574 mol). $K_2CO_3$ (0.844 g, 6.11 mmol) was added and the mixture was cooled down in an ice-salt bath to 0° C. under $N_2$. A 70% solution of TBHP in water (52 mL, 46.8 g 70%≈32.76 g, 0.364 mol) was diluted with acetonitrile (21 mL, 16.51 g, 0.40 mol) and added dropwise to the mixture under $N_2$ at 0° C. in 30 min. Household bleach containing 5.25% NaOCl (260 g, 13.65 g NaOCl, 0.183 mol) was then added over a period of 5 h at −5 to 0° C. After the addition was completed, the reaction mixture was stirred at 0° C. for an additional hour. The product was extracted with hexane (150 mL) and the organic layer was separated. The water layer was washed with hexane (2×100 mL) and the combined organic layer was washed with water (3×150 mL), dried over $Na_2SO_4$, and evaporated to give 20 g of a yellow oil. The crude product was purified by column chromatography (hexane:ethyl acetate, from 98:2 to 92:8) to yield a mixture of (7E,9E)-3-keto-α-ionylideneacetonitrile (23a) and (7E,9Z)-3-keto-α-ionylideneacetonitrile (23b) (7.92 g, 34.54 mmol, 57%) as a yellow oil. The product was shown by HPLC (silica-based nitrile bonded column) and $^1$H- and $^{13}$C-NMR to consist of an isomeric mixture of 7E,9E:7E,9Z=3:1. Crystallization from ethanol at −20° C. gave 23a as a white crystal (5.15 g, 22.46 mmol, 37% isolated yield, m.p.=93-95° C.).

Example 3

Palladium(II)-Mediated Oxidation of (rac)-α-Ionylideneacetonitrile (24a/24b) to (rac)-3-Keto-α-Ionylideneacetonitrile (23a/23b) with Anhydrous TBHP A solution of (rac)-α-Ionylideneacetonitrile (19.60 g, 91.02 mmol) in dichloromethane (150 mL) in a 500 mL three-necked flask was cooled down in an ice-salt bath to 0° C. under $N_2$ and was treated with $K_2CO_3$ (8.4 g, 60.78 mmol) and Pd/C (10 wt. % on C, 7.5 g~0.75 g Pd, 7.05 mmol). A 5.5 M anhydrous solution of TBHP in decane (100 mL, 0.55 mol) was added to the mixture dropwise while maintaining the temperature at 0° C. The mixture was stirred for 36 h at 0° C. and 50 h at R.T. under $N_2$. The solids were removed by filtration through celite and the filtrate was washed with water (3×150 mL), brine, and dried over $Na_2SO_4$. The solvent was removed under reduced pressure to give 24 g of a yellow oil. The crude product was purified by column chromatography (hexane:ethyl acetate, from 98:2 to 92:8) to yield a mixture of 23a and 23b (11.05 g, 48.18 mmol, 53%) as a yellow oil. The product was shown by HPLC and $^1$H- and $^{13}$C-NMR to consist of an isomeric mixture of 7E,9E:7E,9Z=3:1. Crystallization from ethanol at −20° C. gave the (7E,9E)-isomer (23a) as a white crystal (6.00 g, 26.20 mmol, 29% isolated yield).

Example 4

Synthesis of (rac)-α-Ionylideneacetonitrile (24a/24b) by Condensation of α-Ionone with Cyanoacetic Acid (Route 2, FIG. 3)

Freshly distilled rac-α-ionone (32.0 g, 0.166 mol) was transferred into a 250 mL three necked flask using cyclohexylamine (55 mL, 47.63 g, 480 mmol). Cyanoacetic acid (17.85 g, 210 mmol) was added and the mixture was heated at 80-85° C. under $N_2$. After 3.5 h, the mixture was allowed to cool down to room temperature and the product was partitioned between hexane (150 mL) and water (150 mL). The organic layer was removed and the aqueous layer was extracted with hexane (50 mL). The combined organic layer was washed with water (3×200 mL), dried over $Na_2SO_4$, and evaporated to dryness to give 33.9 g of a pale yellow oil. The crude product was purified by fractional distillation to yield a mixture of 24a and 24b (b.p.=105-110° C. at 10 mm) as a colorless oil (26.66 g, 0.124 mol, 75%) that was shown by $^1$H- and $^{13}$C-NMR as well as HPLC to consist of 24a (92%) and 24b (8%) [ratio of isomeric mixture: 7E,9E:7E,9Z=11.5:1].

Example 5

Oxidation of (rac)-α-Ionylideneacetonitrile (24a: 24b=11.5:1) to (7E,9E)-3-Keto-α-Ionylideneacetonitrile (23a) by Bleach and Aqueous TBHP (rac)-α-Ionylideneacetonitrile (26.66 g, 123.8 mmol; 24a: 24b=11.5:1) was transferred into a 1 L three-necked flask using acetonitrile (103 mL, 80.96 g, 1.97 mol). $K_2CO_3$ (1.71 g, 12.37 mmol) was added and the mixture was cooled down in an ice-salt bath to 0° C. under $N_2$. A 70% solution of TBHP in water (124 mL, 111.6 g 70%≈78.12 g, 867 mmol) was added dropwise to the mixture under $N_2$ at 0° C. in 30 min. Household bleach containing 5.25% NaOCl (386 g, 20.27 g NaOCl, 272.3 mmol) was then added over a period of 8 h at −5 to 0° C. After the addition was completed, the reaction mixture was stirred at 0° C. for an additional hour. The product was extracted with hexane (200 mL) and the organic layer was separated. The water layer was washed with hexane (2×100 mL) and the combined organic layer was washed with water (3×200 mL), dried over $Na_2SO_4$, and evaporated to give 36.7 g of a yellow oil. The crude product was purified by column chromatography (hexane:ethyl acetate, from 98:2 to 92:8) to yield a mixture of (7E,9E)-3-keto-α-ionylideneacetonitrile (23a) and (7E,9Z)-3-keto-α-ionylideneacetonitrile (23b) (15.05 g, 65.63 mmol, 53%) as a yellow oil. The product was shown by HPLC (silica-based nitrile bonded column) and $^1$H NMR to consist of 23a (92%) and 23b (8%) [ratio of isomeric mixture: 7E,9E:7E,9Z=11.5:1]. Crystallization from ethanol at −20° C. gave 23a as a white crystal (10.5 g, 45.79 mmol, 37% isolated yield, m.p.=93-95° C.).

Example 6

Oxidation of (rac)-α-Ionone to (rac)-3-Keto-α-Ionone by Bleach and Aqueous TBHP (Route 3, FIG. 3)

Freshly distilled (rac)-α-ionone (20.00 g, 104.0 mmol) was transferred into a 500 mL three-necked flask using EtOAc (103 mL, 92.08 g, 1.05 mol). $K_2CO_3$ (1.44 g, 10.42 mmol) was added and the mixture was cooled down in an ice-salt bath to 0° C. under $N_2$. A 70% solution of TBHP in water (89 mL, 80.1 g 70%≈56.07 g, 0.622 mol) was added dropwise to the mixture under $N_2$ at 0° C. in 30 min. Household bleach containing 5.25% NaOCl (295 g, 15.49 g NaOCl, 0.208 mol) was then added over a period of 5 h at −5 to 0° C. After the addition was completed, the reaction mixture was stirred at 0° C. for an additional hour. The organic layer was removed and the water layer was washed with EtOAc (2×100 mL). The combined organic layer was washed with water (2×150 mL), dried over $Na_2SO_4$, and evaporated to give 26.8 g of a yellow oil. The crude product was purified by column chromatography (hexane:acetone, from 98:2 to 92:8) to yield (rac)-3-keto-α-ionone (13.70 g, 66.41 mmol, 64%).

Example 7

Palladium(II)-Mediated Oxidation of (rac)-α-Ionone to (rac)-3-Keto-α-Ionone with Anhydrous TBHP (Route 3, FIG. 3)

Freshly distilled (rac)-α-ionone (1.00 g, 5.20 mmol) in dichloromethane (10 mL) was cooled down in an ice-salt bath to 0° C. under $N_2$ and was treated with $K_2CO_3$ (0.180 g, 1.30 mmol) and Pd/C (10 wt. % on C, 0.150 g~15 mg Pd, 0.14 mmol). A 5.5 M anhydrous solution of TBHP in decane (5 mL, 27.5 mmol) was added to the mixture at 0° C. The mixture was stirred for 24 h at 0° C. and 12 h at R.T. under $N_2$. The solids were removed by filtration through celite and the filtrate was washed with water (3×20 mL), brine, and dried over $Na_2SO_4$. The solvent was removed under reduced pressure to give 1.3 g of a yellow oil. The crude product was purified by column chromatography (hexane:ethyl acetate, from 98:2 to 92:8) to yield (rac)-3-keto-α-ionone (0.57 g, 2.76 mmol, 53%).

Example 8

Synthesis of (rac)-3-Keto-α-Ionylideneacetonitrile (23a/23b) from (rac)-3-Keto-α-Ionone Sodium hydride (0.427 g of 60% suspension in oil ≈0.256 g, 10.67 mmol) was placed in a three-necked flask equipped with a nitrogen inlet and a thermometer and washed with hexane (2×10 mL). TBME (30 ml) was added and the mixture was cooled to 0° C. Diethyl cyanomethylphosphonate (0.964 g of 98% pure, 0.945 g, 5.33 mmol) in 10 mL TBME was added to the suspension at 5-10° C. under $N_2$ and the mixture was allowed to stir at R.T. for 1 h. The reaction mixture was cooled down in an ice bath and (rac)-3-keto-ionone (1 g, 4.85 mmol) in 10 mL TBME was added dropwise in 30 min at 0-5° C. After stirring for 6 hours at R.T., the reaction was quenched with water and the organic layer was removed. The aqueous layer was extracted with TBME (2×20 mL). The combined organic layer was washed with water, dried over $Na_2SO_4$, and evaporated to dryness. The crude product (1.1 g) was purified by column chromatography (hexane:acetone, from 98:2 to 95:5) to yield a mixture of 23a and 23b (0.9 g, 3.92 mmol, 81%) as a pale yellow oil. The product was shown by HPLC as well as $^1H$- and $^{13}C$-NMR to consist of 23a (75%) and 23b (25%) [ratio of isomeric mixture: 7E,9E:7E,9Z=3:1].

Example 9

Reduction of (7E,9E)-3-Keto-α-Ionylideneacetonitrile (23a) to (7E,9E)-3-Hydroxy-α-Ionylideneacetonitrile (19-22) with $NaBH_4$ To a solution of (7E,9E)-3-keto-α-ionylideneacetonitrile (2 g, 8.72 mmol) in 20 mL ethanol and 15 mL water was added $NaBH_4$ (0.66 g, 17.45 mmol) at 0° C. The mixture was allowed to warm up to room temperature, stirred for 24 h, and the product was partitioned between water (30 mL) and ethyl acetate (50 mL). The organic layer was removed and the aqueous layer was extracted with 30 mL of ethyl acetate. The combined organic layer was washed with brine and water, dried over $Na_2SO_4$, and evaporated to dryness. The crude product was purified by column chromatography (hexane:acetone=97:3) to afford 3-hydroxy-α-ionylideneacetonitriles 19-22 (1.95 g, 8.43 mmol, 97%) as a colorless oil. A mixture of 19+20 was separated from 21+22 by semipreparative HPLC and was fully characterized by $^1H$ and $^{13}C$ NMR as well as mass spectrometry and UV-visible spectrophotometry. The isomeric ratio of (19+20):(21+22)=1:1 was established by normal phase HPLC (silica-based nitrile bonded column) of the mixture. Hydroxynitriles 19+20 and 21+22 were each shown by chiral HPLC (hexane, 95%; 2-propanol, 5%; $CH_3CN$, 0.75%) to consist of an approximately 1:1 mixture of enantiomers.

Example 10

Reduction of (7E,9E)-3-Keto-α-Ionylideneacetonitrile (23a) to (7E,9E)-3-Hydroxy-α-Ionylideneacetonitrile (19-22) with Triisobutylaluminum (TIBA)

A solution of (7E,9E)-3-keto-α-ionylideneacetonitrile (23a) (148 mg, 0.65 mmol) in toluene (10 mL) was cooled down to −40° C. under $N_2$ and a solution of triisobutylaluminum (3 mL of 1M in toluene, 3 mmol) was added. The course of the reaction was monitored by HPLC. The mixture was allowed to warm up to R.T. and stirred for 1 h. The reaction was quenched by adding a dilute aqueous solution of HCl (0.5 mL, 5% v/v) followed by water (10 mL). The product was diluted with TBME (10 mL) and washed sequentially with brine and water. The organic layer was dried over $Na_2SO_4$ and evaporated to dryness. The product (143 mg, 0.62 mmol, 95%) was shown by HPLC to consist of two fractions which were separated by semipreparative HPLC and identified in the order of chromatographic elution (silica-based nitrile bonded column) as (7E,9E)-3-hydroxy-α-ionylideneacetonitriles 19+20 (40%) and (7E,9E)-3-hydroxy-α-ionylidene-acetonitriles 21+22 (60%). The identification was accomplished by comparison of the $^1H$- and $^{13}C$-NMR spectra as well as HPLC retention times of the hydroxynitriles with those of authentic samples characterized earlier. Hydroxynitriles 19+20 and 21+22 were each shown by chiral HPLC to consist of an approximately 1:1 mixture of enantiomers.

Example 11

Reduction of (7E,9E)-3-Keto-α-Ionylideneacetonitrile (23a) to (7E,9E)-3-Hydroxy-α-Ionylideneacetonitrile (19-22) with Sodium Borohydride/dl-Tartaric acid A solution of dl-tartaric acid (46 mg, 0.31 mmol) in EtOH (4 mL) was cooled down to 0° C. and was treated with $NaBH_4$ (12 mg, 0.32 mmol). After the evolution of $H_2$ subsided, the mixture was stirred at R.T. for 1 h and was then cooled down to −15° C. and treated with a solution of (7E,9E)-rac-3-keto-α-ionylideneacetonitrile (23a) (72 mg, 0.31 mmol) in EtOH (3 mL). NaBH$_4$ (24 mg, 0.63 mmol) in EtOH (3 mL) was added to the suspension at −15° C. and the course of the reaction was followed by HPLC (silica-based nitrile bonded column). After 2 h, the product was partitioned between water (10 mL) and ethyl acetate (15 mL). The organic layer was removed and the aqueous layer was extracted with ethyl acetate (10 mL). The combined organic layer was washed with water (2×10 mL), dried over Na$_2$SO$_4$, and evaporated to dryness. The crude product (68.0 mg, 0.29 mmol, 94%) was shown by HPLC to consist of two major fractions which were separated by semipreparative HPLC and identified in the order of chromatographic elution as (7E,9E)-3-hydroxy-α-ionylideneacetonitriles 19+20 (70%) and (7E,9E)-3-hydroxy-α-ionylidene-acetonitriles 21+22 (30%). The $^1$H- and $^{13}$C-NMR as well as HPLC retention times of the hydroxynitriles were identical with those of authentic samples of these compounds characterized earlier. Hydroxynitriles 19+20 and 21+22 were each shown by chiral HPLC to consist of an approximately 1:1 mixture of enantiomers.

Example 12

Reduction of (7E,9E)-3-Keto-α-Ionylideneacetonitrile (23a) to (7E,9E)-3-Hydroxy-α-Ionylideneacetonitrile (19-22) with Sodium Borohydride/2,3-Dibenzoyl-d-Tartaric acid A solution of 2,3-dibenzoyl-d-tartaric acid (94 mg, 0.26 mmol) in EtOH (4 mL) was cooled down to 0° C. and was treated with NaBH$_4$ (10 mg, 0.26 mmol). After the evolution of H$_2$ subsided, the mixture was stirred at R.T. for 1 h and was then cooled down to −15° C. and treated with a solution of (7E,9E)-rac-3-keto-α-ionylideneacetonitrile (23a) (60 mg, 0.26 mmol) in EtOH (3 mL). NaBH$_4$ (20 mg, 0.53 mmol) in EtOH (3 mL) was added to the suspension at −15° C. and the course of the reaction was followed by HPLC (silica-based nitrile bonded column). After 2 h, the product was partitioned between water (10 mL) and ethyl acetate (15 mL). The organic layer was removed and the aqueous layer was extracted with ethyl acetate (10 mL). The combined organic layer was washed with water (2×10 mL), dried over Na$_2$SO$_4$, and evaporated to dryness. The crude product (57.8 mg, 0.25 mmol, 96%) was shown by HPLC to consist of a mixture of (7E,9E)-3-hydroxy-α-ionylideneacetonitriles 19+20 (74%) and (7E,9E)-3-hydroxy-α-ionylidene-acetonitriles 21+22 (26%). The $^1$H- and $^{13}$C-NMR spectra as well as HPLC retention times of the hydroxynitriles were identical with those of authentic samples of these compounds characterized earlier. Hydroxynitriles 19+20 and 21+22 were each shown by chiral HPLC to consist of an approximately 1:1 mixture of enantiomers.

Example 13

Reduction of (7E,9E)-3-Keto-α-Ionylideneacetonitrile (23a) to Hydroxynitrile 19-22 with Sodium bis (2-methoxyethoxy)aluminum hydride (RED-AL™)

A solution of (7E,9E)-3-keto-α-ionylideneacetonitrile (23a) (120 mg, 0.524 mmol) in TBME (5 mL) was cooled down to −5° C. under N$_2$, a solution of Red-Al™ (0.18 mL of 0.65 wt. % in toluene, 0.119 g, 0.59 mmol) in TBME (1 mL) was added, and the mixture stirred for 1 h at this temperature. The reaction was quenched by adding water (10 mL) and the product was extracted with TBME (10 mL) and washed sequentially with brine and water. The organic layer was dried over Na$_2$SO$_4$ and evaporated to dryness. The product (115 mg, 0.497 mmol, 95%) was shown by HPLC (silica-based nitrile bonded column) to consist of (7E,9E)-3-hydroxy-α-ionylideneacetonitriles 19+20 (57%) and (7E,9E)-3-hydroxy-α-ionylidene-acetonitriles 21+22 (43%). The identification was accomplished by comparison of the HPLC retention times and UV spectra of the hydroxynitriles obtained by a photodiode array detector with those of authentic samples characterized earlier. Hydroxynitriles 19+20 and 21+22 were each shown by chiral HPLC to consist of an approximately 1:1 mixture of enantiomers.

Example 14

Reduction of (7E,9E)-3-Keto-α-Ionylideneacetonitrile (23a) to Hydroxynitrile 19-22 with Lithium tri-sec-butylborohydride (L-SELECTRIDE™)

A solution of (7E,9E)-3-keto-α-ionylideneacetonitrile (23a) (100 mg, 0.436 mmol) in TBME (5 mL) was cooled down to −30° C. under N$_2$, A solution of L-SELECTRIDE™ (0.52 mL of 1 M in THF, 0.52 mmol) in TBME (1 mL) was added by a gas-tight syringe, and the mixture was stirred at this temperature for 0.5 h. The reaction mixture was treated with 0.5 mL of 3 N NaOH followed by 0.5 mL of 30% H$_2$O$_2$ and stirred at R.T. for 30 min. The product was extracted with TBME (10 mL) and washed sequentially with brine and water, dried over Na$_2$SO$_4$, and evaporated to dryness to give a colorless oil. The product (94 mg, 0.406 mmol, 93%) was shown by HPLC (silica-based nitrile bonded column) to consist of (7E,9E)-3-hydroxy-α-ionylideneacetonitriles 19+20 (55%) and (7E,9E)-3-hydroxy-α-ionylidene-acetonitriles 21+22 (45%). These were identified by comparison of their HPLC retention times and UV spectra obtained by a photodiode array detector with those of authentic samples of these hydroxynitriles characterized earlier. Hydroxynitriles 19+20 and 21+22 were each shown by chiral HPLC to consist of an approximately 1:1 mixture of enantiomers.

Example 15

Reduction of (7E,9E)-3-Keto-α-Ionylideneacetonitrile (23a) to Hydroxynitrile 19-22 with Sodium tri-sec-butylborohydride (N-SELECTRIDE™)

A solution of (7E,9E)-3-keto-α-ionylideneacetonitrile (23a) (100 mg, 0.436 mmol) in TBME (5 mL) was cooled down to −30° C. under N$_2$, A solution of N-SELECTRIDE™ (0.52 mL of 1 M in THF, 0.52 mmol) in TBME (1 mL) was added by a gas-tight syringe, and the mixture was stirred at this temperature for 0.5 h. The product was worked up as in Example 14 to give a mixture of (7E,9E)-3-hydroxy-α-ionylideneacetonitriles 19+20 (71%) and (7E,9E)-3-hydroxy-α-ionylidene-acetonitriles 21+22 (29%) [(94 mg, 0.406 mmol, 92%)]. Hydroxynitriles 19+20 and 21+22 were each shown by chiral HPLC to consist of an approximately 1:1 mixture of enantiomers.

Example 16

Reduction of (7E,9E)-3-Keto-α-Ionylideneacetonitrile (23a) to Hydroxynitrile 19-22 with Potassium tri-sec-butylborohydride (K-SELECTRIDE™)

A solution of (7E,9E)-3-keto-α-ionylideneacetonitrile (23a) (3 g, 13.08 mmol) in TBME (25 mL) was cooled down to −30° C. under $N_2$, A solution of K-SELECTRIDE™ (20 mL of 1 M in THF, 20 mmol) in TBME (10 mL) was added dropwise in 40 min and the mixture was stirred at this temperature for 4 h. The reaction mixture was treated with 15 mL of 3 N NaOH followed by 15 mL of 30% $H_2O_2$ and stirred at R.T. for 30 min. The product was extracted with TBME (10 mL) and washed sequentially with brine and water, dried over $Na_2SO_4$, and evaporated to dryness to give a colorless oil. The product (2.85 g, 12.32 mmol, 94%) was shown by HPLC (silica-based nitrile bonded column) to consist of a mixture of (7E,9E)-3-hydroxy-α-ionylideneacetonitriles 19+20 (86%) and (7E,9E)-3-hydroxy-α-ionylidene-acetonitriles 21+22 (14%). Hydroxynitriles 19+20 and 21+22 were each shown by chiral HPLC to consist of an approximately 1:1 mixture of enantiomers.

Example 17

Reduction of (7E,9E)-3-Keto-α-Ionylideneacetonitrile (23a) to (7E,9E)-3-Hydroxy-α-Ionylideneacetonitrile (19-22) with (R)-2-Methyl-CBS-oxazaborolidine To a solution of (R)-2-methyl-CBS-oxazaborolidine (0.3 mL 1M in toluene, 0.30 mmol) in TBME (4 mL) was added $BH_3$.THF (0.3 mL 1M in THF, 0.30 mmol) at R.T. under $N_2$. The mixture was stirred at R.T. for 20 min and was then cooled down to 0° C. and treated with a solution of (7E,9E)-rac-3-keto-α-ionylideneacetonitrile (23a) (69 mg, 0.30 mmol) in TBME (3 mL). After stiffing the reaction mixture for 1.5 h at 0° C., HPLC (silica-based nitrile bonded column) showed the complete reduction of 23a. The reaction was quenched by slow addition of methanol (1 mL) and the product was diluted with TBME, washed with a saturated solution of $NH_4Cl$, followed by 5% $NaHCO_3$, and then brine. The organic layer was washed with water (10 mL), dried over $Na_2SO_4$, and evaporated to dryness. The crude product (66.6 mg, 0.29 mmol, 97%) was shown by HPLC to consist of a mixture of (7E,9E)-3-hydroxy-α-ionylideneacetonitriles 19+20 (14%) and (7E,9E)-3-hydroxy-α-ionylideneacetonitriles 21+22 (86%). The hydroxynitriles 19+20 and 21+22 were each shown by chiral HPLC to consist of an approximately 1:1 mixture of enantiomers.

Example 18

Reduction of (7E,9E)-3-Keto-α-Ionylideneacetonitrile (23a) to (7E,9E)-3-Hydroxy-α-Ionylideneacetonitrile (19-22) with (S)-2-Methyl-CBS-oxazaborolidine To a solution of (R)-2-methyl-CBS-oxazaborolidine (0.3 mL 1M in toluene, 0.30 mmol) in TBME (4 mL) was added $BH_3$.THF (0.3 mL 1M in THF, 0.30 mmol) at R.T. under $N_2$. The mixture was stirred at R.T. for 20 min and was then cooled down to 0° C. and treated with a solution of (7E,9E)-rac-3-keto-α-ionylideneacetonitrile (23a) (69 mg, 0.30 mmol) in TBME (3 mL). The product was worked up as described above to give a colorless oil (65 mg, 0.28 mmol, 93%) was shown by HPLC to consist of a mixture of (7E,9E)-3-hydroxy-α-ionylideneacetonitriles 19+20 (25%) and (7E,9E)-3-hydroxy-α-ionylideneacetonitriles 21+22 (75%). The hydroxynitriles 19+20 and 21+22 were each shown by chiral HPLC to consist of an approximately 1:1 mixture of enantiomers.

Example 19

Reduction of Hydroxynitriles 19-22 to Hydroxyaldehydes 15-18 with DIBAL-H

A solution of hydroxynitriles 19+20 (86%) and 21+22 (14%) [2.31 g, 10 mmol] in $CH_2Cl_2$ (10 mL) was cooled down to −40° C. under $N_2$ and a 1M solution of DIBAL-H in $CH_2Cl_2$ (33 mL, 33 mmol) was added dropwise in one hour. After the addition was completed, the reaction mixture was allowed to stir at −30° C. for 1 h. The mixture was then treated with a very slow addition of a homogeneous mixture of 26 g of water absorbed on n-silica (0.3 g of water/g of silica) at a rate that the temperature remained below −10° C. [caution: the addition of silica/water results in rapid elevation of the temperature]. After the addition was completed, the reaction mixture was allowed to stir at 0° C. for 2 h. $Na_2SO_4$ (3 g) was added and the solids were filtered off and washed with $CH_2Cl_2$ (20 mL). The organic layer was washed with water, dried over $Na_2SO_4$, and evaporated to dryness to give a pale yellow oil (2.7 g). Column chromatography (hexane:ethyl acetate, 95:5 to 80:20) of the product gave two fractions as 15+16 (1.155 g, 4.93 mmol, 49%) and 17+18 (0.493 g, 2.1 mmol, 21%).

Example 20

One-Pot Reduction of (7E,9E)-3-Keto-α-Ionylideneacetonitrile (23a) to Hydroxyaldehydes 15-18 with Potassium tri-sec-butylborohydride (K-SELECTRIDE™) Followed by DIBAL-H A solution of (7E,9E)-3-keto-α-ionylideneacetonitrile (23a) (1.2 g, 5.23 mmol) in TBME (10 mL) was cooled down to −30° C. under $N_2$, A solution of K-SELECTRIDE™ (7.6 mL of 1 M in THF, 7.6 mmol) in TBME (5 mL) was added dropwise in 30 min and the mixture was stirred at this temperature and the course of the reaction was monitored by HPLC (silica-based nitrile bonded column). After 2 h, 23a was shown by HPLC to have converted to a mixture of (7E,9E)-3-hydroxy-α-ionylideneacetonitriles 19+20 (86%) and (7E,9E)-3-hydroxy-α-ionylideneacetonitriles 21+22 (14%). The reaction mixture was then treated with a 1M solution of DIBAL-H in $CH_2Cl_2$ (13 mL, 13 mmol) dropwise in 30 minutes. After the addition was completed, the reaction mixture was allowed to stir at −20° C. for 3 h. The product was then treated with a very slow addition of a homogeneous mixture of 20 g of water absorbed on n-silica (0.5 g of water/g of silica) at a rate that the temperature remained below −10° C. [caution: the addition of silica/water results in rapid elevation of the temperature]. The reaction mixture was allowed to stir at 0° C. for 2 h. $Na_2SO_4$ (3 g) was added and the solids were filtered off and washed with $CH_2Cl_2$ (20 mL). The organic layer was washed with water, dried over $Na_2SO_4$, and evaporated to dryness to give a pale yellow oil (1.9 g). Column chromatography (hexane:ethyl acetate, 95:5 to 80:20) of the product gave two fractions as 15+16 (0.942 g, 4.0 mmol, 77%) and 17+18 (0.077 g, 0.33 mmol, 6%).

Example 21

Oxidative Degradation of (3R,3'R,6'R)-Lutein Diacetate to (3R,6R)-3-hydroxy-13-apo-ε-caroten-13-one (27) and (3R)-3-hydroxy-13-apo-β-caroten-13-one (28)

Preparation of (3R,3'R,6'R)-Lutein Diacetate. Naturally occurring (3R,3'R,6'R)-lutein was obtained from Kemin Health (Des Moines, Iowa) and converted to (3R,3'R,6'R)-lutein diacetate as follows. A solution of (3R,3'R,6'R)-lutein (3 g, 75% pure ≈2.25 g, 3.96 mmol) in 20 mL of THF was treated with pyridine (2.5 mL, 2.45 g, 30.97 mmol) and acetic anhydride (2.5 mL, 2.71 g, 26.55 mmol) and the mixture was heated at 45° C. under $N_2$ overnight. The product was partitioned between water (50 mL) and hexane (50 mL). The organic layer was removed and washed sequentially with 50 mL of aqueous HCl (5%, v/v), 50 mL of saturated sodium bicarbonate solution, and water (50 mL). The organic layer was dried over $Na_2SO_4$ and evaporated to dryness to give a red solid which was purified by column chromatography on n-silica (hexane:acetone, from 90:10 to 70:30) to give lutein diacetate (2.30 g, 3.52 mmol; 89%).

Oxidative Degradation of (3R,3'R,6'R)-Lutein Diacetate. A solution of (3R,3'R,6'R)-lutein diacetate (1 g, 1.53 mmol) in ethyl acetate (30 mL) was cooled down in an ice-salt bath to 0° C. under $N_2$ and was treated with a 70% solution of TBHP in water (2.70 mL, 2.43 g 70%≈1.70 g, 18.86 mmol). Household bleach containing 5.25% NaOCl (8.84 g, 0.464 g NaOCl, 6.23 mmol) was then added over a period of 20 min at 0° C. After the addition was completed, the reaction mixture was allowed to warm up to R.T. and stirred for 3 h. The organic layer was removed and the water layer was washed with EtOAc (2×100 mL). The combined organic layer was washed with water (2×150 mL), dried over $Na_2SO_4$, and evaporated to dryness. The residue was dissolved in dichloromethane (30 mL) and saponified with KOH/MeOH (30 mL, 10%, wt/v) at R.T. under $N_2$. After 2 h, the product was washed with water (3×100 mL), dried over $Na_2SO_4$, and evaporated to dryness. Purification by column chromatography on n-silica (hexane:acetone, from 95:5 to 70:30) followed by semipreparative HPLC (nitrile bonded column) afforded two major products which were fully characterized from their UV-Vis, CD, $^1$H- and $^{13}$C-NMR, and mass spectra as (3R,6R)-3-hydroxy-13-apo-ε-caroten-13-one (27) and (3R)-3-hydroxy-13-apo-β-caroten-13-one (28).

Example 22

Enzyme-Mediated Acylation of (7E,9E)-3-Hydroxy-α-Ionylideneacetaldehydes 15+16 with Lipase AK (*pseudomonas fluorescens*)

To a solution of (7E,9E)-3-hydroxy-α-ionylideneacetaldehydes 15+16 (2.4 g, 10.32 mmol) in 20 mL of pentane was added 1.5 g of lipase AK (*pseudomonas fluorescens*) and vinyl acetate (2.84 mL, 2.65 g, 30.78 mmol). The mixture was refluxed (35-36° C.) under $N_2$ and the course of the enzymatic acylation was monitored by chiral HPLC (2-propanol, 2%; $CH_3CN$, 98%). After 48 h, the product was filtered through celite and the filtrate was evaporated to dryness to give a yellow oil (2.7 g). Column chromatography (hexane:ethyl acetate, 98:2 to 85:15) of the product gave two major fractions.

The first fraction was tentatively identified from its $^1$H NMR and UV spectrum as (3S,6S)-3-acetoxy-α-ionylideneacetaldehyde (25) [1.22 g, 4.41 mmol, 43%]. This fraction was dissolved in $CH_2Cl_2$ (25 mL) and treated with KOH/MeOH (2.3 mL, 10% wt/v) for 2 h at 0° C. The product was washed with water (3×50 mL), dried over $Na_2SO_4$, and evaporated to dryness. The product was fully characterized from its UV, CD, $^1$H- and $^{13}$C-NMR, and mass spectra as (3S,6S)-3-hydroxy-α-ionylideneacetaldehyde (16) (1.00 g, 4.27 mmol; 97%). The optical purity of 16 (93% ee) was established by chiral HPLC.

The second fraction was fully characterized from its UV, CD, $^1$H- and $^{13}$C-NMR, and mass spectra as (3R,6R)-3-hydroxy-α-ionylideneacetaldehyde (15) (1.03 g, 4.40 mmol, 43%). The optical purity of 15 (94% ee) was established by chiral HPLC.

The absolute configuration of hydroxyaldehydes 15 and 16 was assigned from comparison of their $^1$H NMR and CD spectra with those of $C_{18}$-ketone 27.

Example 23

Enzyme-Mediated Acylation of (7E,9E)-3-Hydroxy-α-Ionylideneacetaldehydes 17+18 with Lipase AK (*pseudomonas fluorescens*)

To a solution of (7E,9E)-3-hydroxy-α-ionylideneacetaldehydes 17+18 (0.843 g, 3.60 mmol) in 20 mL of pentane was added 0.58 g of lipase AK (*pseudomonas fluorescens*) and vinyl acetate (1.4 mL, 1.31 g, 15.22 mmol). The mixture was refluxed (35-36° C.) under $N_2$ and the course of the enzymatic acylation was monitored by chiral HPLC (2-propanol, 2%; $CH_3CN$, 98%). After 50 h, the product was filtered through celite and the filtrate was evaporated to dryness to give a yellow oil (1.0 g). Column chromatography (hexane:ethyl acetate, 98:2 to 85:15) of the product gave two major fractions.

The first fraction was tentatively identified from its $^1$H NMR and UV spectrum as (3S,6R)-3-acetoxy-α-ionylideneacetaldehyde (26) [0.319 g, 1.15 mmol, 32%]. This fraction was dissolved in $CH_2Cl_2$ (25 mL) and hydrolyzed with KOH/MeOH (0.8 mL, 10% wt/v) for 2 h at 0° C. The product was worked up as in Example 21 and was fully characterized from its UV, CD, $^1$H- and $^{13}$C-NMR, and mass spectra as (3S,6R)-3-hydroxy-α-ionylidene-acetaldehyde (17) (0.267 g, 1.14 mmol; 99%). The optical purity of 17 (91% ee) was established by chiral HPLC.

The second fraction was fully characterized from its UV, CD, $^1$H and $^{13}$C-NMR, and mass spectra as (3R,6S)-3-hydroxy-α-ionylideneacetaldehyde (18) (0.31 g, 1.32 mmol, 37%). The optical purity of 18 (92% ee) was established by chiral HPLC.

The absolute configuration of hydroxyaldehydes 17 and 18 was assigned from comparison of their $^1$H NMR and CD spectra with those of $C_{18}$-ketone 27.

Example 24

Preparation of (all-E)-(7-Fomyl-2-methyl-2,4,6-octatrienyl)-triphenyl phosphonium chloride dimethyl acetal (14)

(all-E)-(7-Fomyl-2-methyl-2,4,6-octatrienyl)triphenyl phosphonium chloride was prepared according to the method developed by Bernhard et al. (*Helv. Chim. Acta* 1980, 63: 1473-1490) and was freshly converted to its dimethyl acetal (14) prior to Wittig condensation reactions. A mixture of (all-E)-(7-formyl-2-methyl-2,4,6-octatrienyl)triphenyl phosphonium chloride (1.36 g, 3.04 mmol), trimethylorthoformate (0.38 g, 3.58 mmol), p-TsOH (6 mg) in methanol (20 mL) was stirred for 3 h at 30° C. The mixture was treated with a few drops of N,N-diisopropylethylamine (DIPEA) and concentrated on a rotary evaporator below 40° C. The concentrated solution of the protected Wittig salt 14 (1.42 g, 2.88 mmol, 95%) in methanol was directly used in the coupling reactions without purification.

Example 25

General Procedure for the Synthesis of $C_{25}$-hydroxy-aldehydes 6-9 Synthesis of (3R,6R)-3-Hydroxy-12'-apo-ε-caroten-12'-al (6)

A solution of (3R,6R)-3-hydroxy-α-ionylideneacetaldehyde (15) (250.4 mg, 1.07 mmol) in MeOH (3 mL) was treated with a solution of the protected Wittig salt 14 (817.7 mg, 1.66 mmol) in methanol (2 mL) at R.T. under $N_2$. 1 mL of a 0.42 M solution of NaOMe (0.42 mmol) in MeOH (freshly prepared from Na in MeOH) was added and the mixture was stirred at R.T. for 4 h. The product was partitioned between water (50 mL) and $CH_2Cl_2$ (30 mL), the organic layer was removed, and the water layer was extracted with $CH_2Cl_2$ (20 mL). The combined organic layer was washed with water (2×30 mL), dried over $Na_2SO_4$, and evaporated to dryness to give a red solid (1.3 g). A small quantity of the solid was purified by semipreparative HPLC and identified from its UV-visible, $^1$H- and $^{13}$C-NMR, and mass spectra as (3R,6R)-3-hydroxy-12'-apo-ε-caroten-12'-al dimethyl acetal (10). The red solids were dissolved in acetone (4 mL) and water (1 mL) and stirred with 0.075 mL of 0.3 N HCl for 1 h at R.T. under $N_2$. The product was extracted with $CH_2Cl_2$, and sequentially washed with saturated solution of $NaHCO_3$ and water, dried over $Na_2SO_4$, and evaporated to dryness to give a red oil. Column chromatography (hexane:ethyl acetate, 95:5 to 80:20) gave a red solid that was identified from its UV-visible, CD, $^1$H- and $^{13}$C-NMR, and mass spectra as (3R,6R)-3-hydroxy-12'-apo-ε-caroten-12'-al (6) (334 mg, 0.91 mmol; 85%).

Following the above procedure, (3S,6S)-3-hydroxy-12'-apo-ε-caroten-12'-al (7), (3S,6R)-3-hydroxy-12'-apo-ε-caroten-12'-al (8), and (3R,6S)-3-hydroxy-12'-apo-ε-caroten-12'-al (9) were prepared in yields ranging from 75-85%.

Example 26

General Procedure for the Synthesis of Luteins 1-4 Synthesis of (3R,3'R,6'R)-Lutein (1)

A solution of (3R,6R)-3-hydroxy-12'-apo-ε-caroten-12'-al (6) (257 mg, 0.70 mmol) and (3R)-3-hydroxy-(β-ionylideneethyl)triphenylphosphonium chloride (Wittig salt 5) (410 mg, 0.79 mmol) in $CH_2Cl_2$ (5 mL) was cooled down to −5° C. under $N_2$. A solution of KOH (130 mg, 2.32 mmol) in $H_2O$ (0.5 mL) was added and the mixture was stirred for 0.5 h at −5° C. and 3 h at R.T. Dichloromethane (20 mL) was added, and the product was washed with water (3×10 mL). The organic layer was removed, dried over $Na_2SO_4$, and evaporated to dryness to give 1 g of a red oil. The crude product was then refluxed in ethyl acetate for 4 h under $N_2$ to affect the cis (Z) to trans (E) thermal isomerization of lutein. After solvent evaporation, the product was purified by column chromatography (hexane:ethylacetate, from 90:10 to 50:50) to give a red solid that was crystallized from hexane:acetone=4:1 and identified from its UV-visible, CD, $^1$H- and $^{13}$C-NMR, and mass spectra as (3R,3'R,6'R)-Lutein (1) (0.294 g, 0.517 mmol; 74%).

Following the above procedure, (3R,3'S,6'S)-lutein (2), (3R,3'S,6'R)-lutein or 3'-epilutein (3), and (3R,3'R,6'S)-lutein (4) were prepared in yields ranging from 65-74%.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method for synthesis of a compound having the Formula (I):

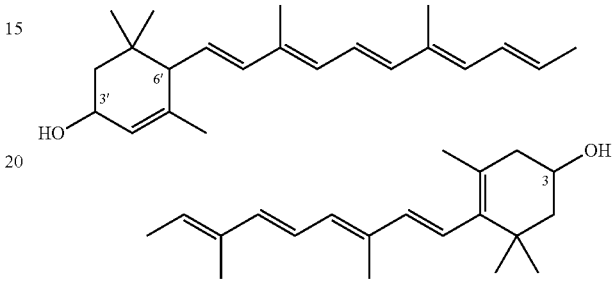

comprising reacting a compound having the Formula (II):

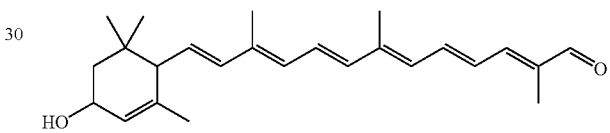

with a compound having the Formula (III):

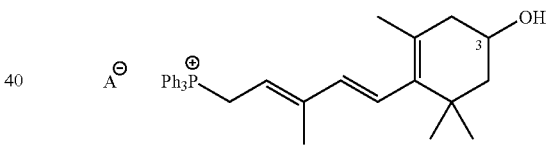

via Wittig coupling, wherein $A^\ominus$ is an anionic counterion.

2. The method of claim 1, wherein said compound of Formula (I) is (3R,3'R,6'R)-lutein, (3R,3'S,6'S)-lutein, (3R,3'S,6'R)-lutein, (3R,3'R,6'S)-lutein, (3S,3'S,6'S)-lutein, (3S,3'R,6'R)-lutein, (3S,3'R,6'S)-lutein, (3S,3'S,6'R)-lutein, or a combination thereof.

3. The method of claim 1, wherein said compound of Formula (III) is (3R)-3-hydroxy-(β-ionylideneethyl)triphenylphosphonium salt or (3S)-3-hydroxy-(β-ionylideneethyl)triphenylphosphonium salt.

4. The method of claim 3, wherein said salt is the chloride, bromide or iodide salt.

5. The method of claim 1, wherein the compound of Formula II is prepared by a process comprising deprotecting a compound having the Formula (IV):

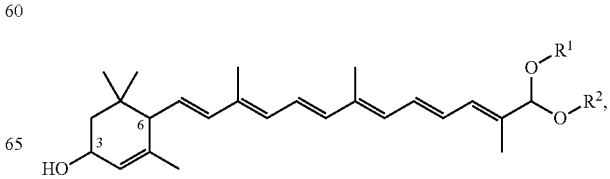

to obtain said compound having the Formula II, wherein $R^1$ and $R^2$ are independently a branched $C_1$-$C_7$ alkyl, a straight chain $C_1$-$C_7$ alkyl, or taken together form a 5-7 membered ring.

6. The method of claim 5, wherein said compound having the Formula (IV) is deprotected under mild acidic conditions without loss of optical purity.

7. The method of claim 5, wherein $R^1$ and $R^2$ are independently $C_1$-$C_7$ alkyl.

8. The method of claim 7, wherein $R^1$ and $R^2$ are methyl.

9. The method of claim 5, wherein said compound having the Formula (II) is (3R,6R)-3-hydroxy-12'-apo-ε-caroten-12'-al, (3S,6S)-3-hydroxy-12'-apo-ε-caroten-12'-al, (3S,6R)-3-hydroxy-12'-apo-ε-caroten-12'-al, (3R,6S)-3-hydroxy-12'-apo-ε-caroten-12'-al, or a combination thereof.

10. The method of claim 9, wherein
(i) (3R,6R)-3-hydroxy-12'-apo-ε-caroten-12'-al dimethylacetal is deprotected to form (3R,6R)-3-hydroxy-12'-apo-ε-caroten-12'-al;
(ii) (3S,6S)-3-hydroxy-12'-apo-ε-caroten-12'-al dimethylacetal is deprotected to form (3S,6S)-3-hydroxy-12'-apo-ε-caroten-12'-al;
(iii) (3S,6R)-3-hydroxy-12'-apo-ε-caroten-12'-al dimethyl acetal is deprotected to form (3S,6R)-3-hydroxy-12'-apo-ε-caroten-12'-al; or
(iv) (3R,6S)-3-hydroxy-12'-apo-ε-caroten-12'-al dimethylacetal is deprotected to form (3R,6S)-3-hydroxy-12'-apo-ε-caroten-12'-al.

11. The method of claim 5, wherein the compound of Formula IV is prepared by a process comprising elongating a compound having the Formula V:

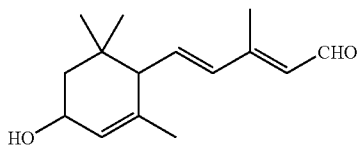

with a compound having the Formula VI:

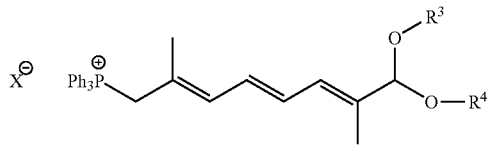

via Wittig coupling to obtain said compound having the Formula IV, where $X^\ominus$ is an anionic counterion, wherein $R^3$ and $R^4$ are independently a branched $C_1$-$C_7$ alkyl, a straight chain $C_1$-$C_7$ alkyl, or taken together form a 5-7 membered ring.

12. The method of claim 11, wherein $R^1$ and $R^2$ are independently $C_1$-$C_7$ alkyl.

13. The method of claim 12, wherein $R^1$ and $R^2$ are methyl.

14. The method of claim 11, wherein said compound having the Formula (IV) is (3R,6R)-3-hydroxy-12'-apo-ε-caroten-12'-al dimethylacetal, (3S,6S)-3-hydroxy-12'-apo-ε-caroten-12'-al dimethylacetal, (3S,6R)-3-hydroxy-12'-apo-ε-caroten-12'-al dimethyl acetal, (3R,6S)-3-hydroxy-12'-apo-ε-caroten-12'-al dimethylacetal, or a combination thereof.

15. The method of claim 11, wherein said compound having the Formula (VI) is (all-E)-(7-formyl-2-methyl-2,4,6-octatrienyl)triphenylphosphonium salt.

16. The method of claim 15, wherein said salt is the chloride, bromide or iodide salt.

17. The method of claim 14, wherein
(i) (all-E)-(7-formyl-2-methyl-2,4,6-octatrienyl)triphenylphosphonium salt is reacted with (7E,9E,3R,6R)-3-hydroxy-α-ionylideneacetaldehyde to obtain (3R,6R)-3-hydroxy-12'-apo-ε-caroten-12'-al dimethylacetal;
(ii) (all-E)-(7-formyl-2-methyl-2,4,6-octatrienyl)triphenylphosphonium salt is reacted with (7E,9E,3S,6S)-3-hydroxy-α-ionylideneacetaldehyde to obtain (3S,6S)-3-hydroxy-12'-apo-ε-caroten-12'-al dimethylacetal;
(iii) (all-E)-(7-formyl-2-methyl-2,4,6-octatrienyl)triphenylphosphonium salt is reacted with (7E,9E,3S,6R)-3-hydroxy-α-ionylideneacetaldehyde to obtain (3S,6R)-3-hydroxy-12'-apo-ε-caroten-12'-al dimethyl acetal; or
(iv) (all-E)-(7-formyl-2-methyl-2,4,6-octatrienyl)triphenylphosphonium salt is reacted with (7E,9E,3R,6S)-3-hydroxy-α-ionylideneacetaldehyde to obtain (3R,6S)-3-hydroxy-12'-apo-ε-caroten-12'-al dimethylacetal.

18. The method of claim 11, wherein the compound of Formula V is prepared by a process comprising reacting the cyano group of a compound having the Formula VII:

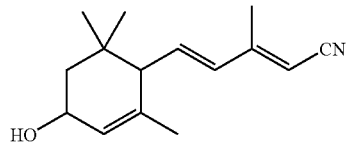

with a reducing agent to obtain said compound having the Formula V:

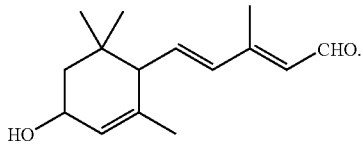

19. The method of claim 18, wherein said compound having the Formula (V) is (7E,9E,3R,6R)-3-hydroxy-α-ionylideneacetaldehyde, (7E,9E,3S,6S)-3-hydroxy-α-ionylideneacetaldehyde, (7E,9E,3S,6R)-3-hydroxy-α-ionylideneacetaldehyde, (7E,9E,3R,6S)-3-hydroxy-α-ionylideneacetaldehyde, or a combination thereof.

20. The method of claim 18, wherein said compound having the Formula (VII) is (3R,6R)-3-hydroxy-α-ionylideneacetonitrile, (3S,6S)-3-hydroxy-α-ionylideneacetonitrile, (3S,6R)-3-hydroxy-α-ionylideneacetonitrile, (3R,6S)-3-hydroxy-α-ionylideneacetonitrile, or a combination thereof.

21. The method of claim 20, wherein a mixture of (3R,6R)-3-hydroxy-α-ionylideneacetonitrile, (3S,6S)-3-hydroxy-α-ionylideneacetonitrile, (3S,6R)-3-hydroxy-α-ionylideneacetonitrile, and (3R,6S)-3-hydroxy-α-ionylideneacetonitrile is reduced with diisobutylaluminum hydride (DIBAL-H), to obtain a mixture of (7E,9E,3R,6R)-3-hydroxy-α-ionylideneacetaldehyde, (7E,9E,3S,6S)-3-hydroxy-α-ionylideneacetaldehyde, (7E,9E,3S,6R)-3-hydroxy-α-ionylideneacetaldehyde, and (7E,9E,3R,6S)-3-hydroxy-α-ionylideneacetaldehyde.

22. The method of claim 21, further comprising separating a mixture of (7E,9E,3R,6R)-3-hydroxy-α-ionylideneacetaldehyde, (7E,9E,3S,6S)-3-hydroxy-α-ionylideneacetaldehyde, (7E,9E,3S,6R)-3-hydroxy-α-ionylideneacetaldehyde, (7E,9E,3R,6S)-3-hydroxy-α-ionylideneacetaldehyde, or a combination thereof using a combination of column chromatography and enzyme-mediated acylation.

23. The method of claim 22, wherein a mixture of (7E,9E,3R,6R)-3-hydroxy-α-ionylideneacetaldehyde and (7E,9E,3S,6S)-3-hydroxy-α-ionylideneacetaldehyde is separated from said mixture of (7E,9E,3R,6R)-3-hydroxy-αionylideneacetaldehyde, (7E,9E,3S,6S)-3-hydroxy-α-ionylideneacetaldehyde, (7E,9E,3S,6R)-3-hydroxy-α-ionylideneacetaldehyde, and (7E,9E,3R,6S)-3-hydroxy-α-ionylideneacetaldehyde by silica gel chromatography using a combination of a hydrocarbon solvent selected from the group consisting of pentane, hexane, heptane and cyclohexane, and ethyl acetate or acetone, to obtain a mixture of (7E,9E,3R,6R)-3-hydroxy-α-ionylideneacetaldehyde and (7E,9E,3S,6S)-3-hydroxy-α-ionylideneacetaldehyde.

24. The method of claim 22, wherein a mixture of (7E,9E,3S,6R)-3-hydroxy-α-ionylideneacetaldehyde and (7E,9E,3R,6S)-3-hydroxy-α-ionylideneacetaldehyde is separated from said mixture of (7E,9E,3R,6R)-3-hydroxy-αionylideneacetaldehyde, (7E,9E,3S,6S)-3-hydroxy-α-ionylideneacetaldehyde, (7E,9E,3S,6R)-3-hydroxy-α-ionylideneacetaldehyde, and (7E,9E,3R,6S)-3-hydroxy-α-ionylideneacetaldehyde by silica gel chromatography using a combination of a hydrocarbon solvent selected from the group consisting of pentane, hexane, heptane and cyclohexane, and ethyl acetate or acetone, to obtain a mixture of (7E,9E,3S,6R)-3-hydroxy-α-ionylideneacetaldehyde and (7E,9E,3R,6S)-3-hydroxy-α-ionylideneacetaldehyde.

25. The method of claim 23, further comprising acylating said mixture of (7E,9E,3R,6R)-3-hydroxy-α-ionylideneacetaldehyde and (7E,9E,3S,6S)-3-hydroxy-α-ionylideneacetaldehyde with lipase AK (*Pseudomonas fluorescens*) or lipase PS (*Pseudomonas cepacia*) in the presence of an acyl donor, wherein (7E,9E,3S,6S)-3-hydroxy-α-ionylideneacetaldehyde is converted to (3S,6S)-3-acetoxy-α-ionylideneacetaldehyde while (7E,9E,3R,6R)-3-hydroxy-α-ionylideneacetaldehyde remains unesterified.

26. The method of claim 25, wherein said acyl donor is vinyl acetate.

27. The method of claim 25, further comprising saponifying (3S,6S)-3-acetoxy-α-ionylideneacetaldehyde with alcoholic potassium hydroxide (KOH) or sodium hydroxide (NaOH) to obtain (7E,9E,3S,6S)-3-hydroxy-α-ionylideneacetaldehyde.

28. The method of claim 24, further comprising acylating said mixture of (7E,9E,3S,6R)-3-hydroxy-α-ionylideneacetaldehyde and (7E,9E,3R,6S)-3-hydroxy-α-ionylideneacetaldehyde with lipase AK (*Pseudomonas fluorescens*) or lipase PS (*Pseudomonas cepacia*) in the presence of an acyl donor, wherein (7E,9E,3S,6R)-3-hydroxy-α-ionylideneacetaldehyde is converted to (3S,6R)-3-acetoxy-α-ionylideneacetaldehyde while (7E,9E,3R,6S)-3-hydroxy-α-ionylideneacetaldehyde remains unesterified.

29. The method of claim 28, wherein said acyl donor is vinyl acetate.

30. The method of claim 28, further comprising saponifying (3S,6R)-3-acetoxy-α-ionylideneacetaldehyde with alcoholic potassium hydroxide (KOH) or sodium hydroxide (NaOH) to obtain (7E,9E,3S,6R)-3-hydroxy-α-ionylideneacetaldehyde.

31. The method of claim 18, further comprising reducing the ketone group of a compound having the Formula (VIII):

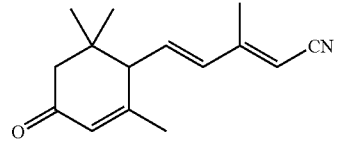

with a reducing agent, to obtain said compound having the Formula (VII):

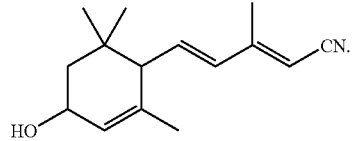

32. The method of claim 31, wherein said compound having the Formula (VIII) is (7E,9E)-3-keto-α-ionylideneacetonitrile, (7E,9Z)-3-keto-α-ionylideneacetonitrile, or a combination thereof.

33. The method of claim 31, wherein said compound having the Formula (VII) is (3R,6R)-3-hydroxy-α-ionylideneacetonitrile, (3S,6S)-3-hydroxy-α-ionylideneacetonitrile, (3S,6R)-3-hydroxy-α-ionylideneacetonitrile, (3R,6S)-3-hydroxy-α-ionylideneacetonitrile, or a combination thereof.

34. The method of claim 31, wherein said reducing agent is stereoselective.

35. The method of claim 32, wherein (7E,9E)-3-keto-α-ionylideneacetonitrile is stereoselectively reduced with a reducing agent to obtain (3,6-trans)-$C_{15}$-hydroxynitriles (3R,6R)-3-hydroxy-α-ionylideneacetonitrile and (3S,6S)-3-hydroxy-α-ionylideneacetonitrile and (3,6-cis)-$C_{15}$-hydroxynitriles (3S,6R)-3-hydroxy-α-ionylideneacetonitrile and (3R,6S)-3-hydroxy-α-ionylideneacetonitrile in a ratio ranging from 6:1 to 1:6.

36. The method of claim 35, wherein said reducing agent is $NaBH_4$, $NaBH_4$/dl-tartaric acid, $NaBH_4$/d-tartaric acid, $NaBH_4$/l-tartaric acid, $NaBH_4$/dibenzoyl-d-tartaric acid, $NaAlH_2(OCH_2CH_2OMe)_2$, $LiB[CHMeCH_2CH_3]_3H$, $NaB[CHMeCH_2CH_3]_3H$, $KB[CHMeCH_2CH_3]_3H$, $KB[CHMeCHMe_2]_3H$, $BH_3$/(R)-2-methyl-CBS-oxazaborolidine or $BH_3$/(S)-2-methyl-CBS-oxazaborolidine.

37. The method of claim 36, wherein (7E,9E)-3-keto-α-ionylideneacetonitrile is selectively reduced with $KB[CHMeCH_2CH_3]_3H$ to obtain (3R,6R)-3-hydroxy-α-ionylideneacetonitrile and (3S,6S)-3-hydroxy-α-ionylideneacetonitrile as the major products and (3S,6R)-3-hydroxy-α-ionylideneacetonitrile and (3R,6S)-3-hydroxy-α-ionylideneacetonitrile as the minor products.

38. The method of claim 36, wherein (7E,9E)-3-keto-α-ionylideneacetonitrile is selectively reduced with $BH_3$/(R)-2-methyl-CBS-oxazaborolidine to obtain (3S,6R)-3-hydroxy-α-ionylideneacetonitrile and (3R,6S)-3-hydroxy-α-ionylideneacetonitrile as the major products and (3R,6R)-3-hydroxy-α-ionylideneacetonitrile and (3S,6S)-3-hydroxy-α-ionylideneacetonitrile as the minor products.

39. The method of claim 32, further comprising
(i) reducing (7E,9E)-3-keto-α-ionylideneacetonitrile with a metal hydride reagent to form a mixture of (3R,6R)-3-hydroxy-α-ionylideneacetonitrile, (3S,6S)-3-hydroxy-α-ionylideneacetonitrile, (3S,6R)-3-hydroxy-α-ionylideneacetonitrile, and (3R,6S)-3-hydroxy-α-ionylideneacetonitrile; and (ii) reducing said mixture with DIBAL-H to obtain a mixture of (7E,9E,3R,6R)-3-hydroxy-α-ionylideneacetaldehyde, (7E,9E,3S,6S)-3-hydroxy-α-ionylideneacetaldehyde, (7E,9E,3S,6R)-3-hydroxy-α-ionylideneacetaldehyde, and (7E,9E,3R,6S)-3-hydroxy-α-ionylideneacetaldehyde,
in a one-pot reaction.

40. The method of claim 39, wherein said metal hydride reagent is NaAlH$_2$(OCH$_2$CH$_2$OMe)$_2$, LiB[CHMeCH$_2$CH$_3$]$_3$H, NaB[CHMeCH$_2$CH$_3$]$_3$H, KB[CHMeCH$_2$CH$_3$]$_3$H or KB[CHMeCHMe$_2$]$_3$H.

41. The method of claim 31, wherein the compound of Formula VIII is prepared by a process comprising reacting a compound having the Formula (IX):

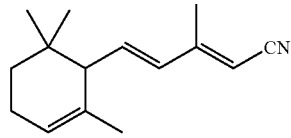

with an oxidizing agent via allylic oxidation, to obtain said compound having the Formula (VIII):

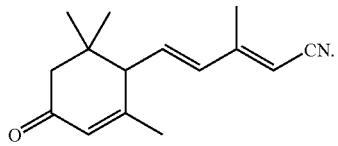

42. The method of claim 41, wherein said compound having the Formula (IX) is (7E,9E)-α-ionylideneacetonitrile, (7E,9Z)-α-ionylideneacetonitrile, or a combination thereof.

43. The method of claim 41, wherein said compound having the Formula (VIII) is (7E,9E)-3-keto-α-ionylideneacetonitrile, (7E,9Z)-3-keto-α-ionylideneacetonitrile, or a combination thereof.

44. The method of claim 42, wherein a mixture of (7E,9E)-α-ionylideneacetonitrile and (7E,9Z)-α-ionylideneacetonitrile in an isomeric ratio ranging from 3:1 to 12:1 is reacted with an oxidizing reagent, to obtain a mixture of (7E,9E)-3-keto-α-ionylideneacetonitrile and (7E,9Z)-3-keto-α-ionylideneacetonitrile in an isomeric ratio ranging from 3:1 to 12:1.

45. The method of claim 44, further comprising separating said mixture of (7E,9E)-3-keto-α-ionylideneacetonitrile and (7E,9Z)-3-keto-α-ionylideneacetonitrile via crystallization with an alcohol, at a temperature ranging from −15 to 0° C.

46. The method of claim 45, wherein said alcohol is ethanol.

47. The method of claim 44, wherein said compound of Formula IX is a mixture of (7E,9E)-α-ionylideneacetonitrile and (7E,9Z)-α-ionylideneacetonitrile in an isomeric ratio ranging from 3:1 to 12:1 and is oxidized with a combination of tert-BuOOH (TBHP) and bleach (5.25% NaOCl), at a temperature ranging from −5 to 0° C., in a solvent selected from the group consisting of acetonitrile (CH$_3$CN), methylene chloride (CH$_2$Cl$_2$), ethyl acetate, hexane, tetrahydrofuran (THF), tert-butyl methyl ether (TBME), dimethylformamide (DMF), dimethylsulfoxide (DMSO), ethylene glycol, a straight chain C$_1$-C$_5$ alcohol and a branched C$_1$-C$_5$ alcohol, to obtain the compound of Formula VIII as a mixture of (7E,9E)-3-keto-α-ionylideneacetonitrile and (7E,9Z)-3-keto-α-ionylideneacetonitrile.

48. The method of claim 44, wherein said compound of Formula IX is a mixture of (7E,9E)-α-ionylideneacetonitrile and (7E,9Z)-α-ionylideneacetonitrile in an isomeric ratio ranging from 3:1 to 12:1 and is oxidized with a combination of tert-BuOOH (TBHP) and Pd/C at a temperature ranging from 0° C. to room temperature (R.T.), in a solvent selected from the group consisting of acetonitrile (CH$_3$CN), methylene chloride (CH$_2$Cl$_2$), ethyl acetate, hexane, tetrahydrofuran (THF), tert-butyl methyl ether (TBME), dimethylformamide (DMF), dimethylsulfoxide (DMSO), ethylene glycol, a straight chain C$_1$-C$_5$ alcohol and a branched C$_1$-C$_5$ alcohol, to obtain the compound of Formula VIII as a mixture of (7E,9E)-3-keto-α-ionylideneacetonitrile and (7E,9Z)-3-keto-α-ionylideneacetonitrile.

49. The method of claim 41, wherein the compound of Formula IX is prepared by a process comprising condensing a compound having the Formula (X):

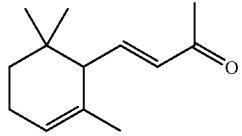

with cyanoacetic acid to obtain said compound having the Formula (IX):

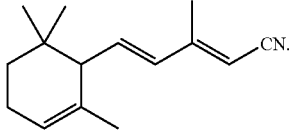

50. The method of claim 49, wherein said compound having the Formula (IX) is (7E,9E)-α-ionylideneacetonitrile, (7E,9Z)-α-ionylideneacetonitrile, or a mixture thereof.

51. The method of claim 49, wherein said compound having the Formula (X) is (rac)-α-ionone.

52. The method of claim 51, (rac)-α-ionone is condensed with cyanoacetic acid in the presence of an amine, at a temperature ranging from 80° C. to 100° C., to obtain (7E,9E)-α-ionylidene-acetonitrile and (7E,92)-α-ionylideneacetonitrile in a ratio of 12:1 or greater.

53. The method of claim 52, wherein said amine is cyclohexylamine.

54. The method of claim 52, further comprising purifying said mixture of (7E,9E)-α-ionylidene-acetonitrile and (7E,9Z)-α-ionylideneacetonitrile in an isomeric ratio of 12:1 or greater by vacuum distillation, wherein said isomeric ratio of (7E,9E)-α-ionylidene-acetonitrile and (7E,9Z)-α-ionylideneacetonitrile is unaltered.

55. A method comprising reacting (rac)-α-ionone with a combination of tert-BuOOH (TBHP) and bleach, at a temperature ranging from −5 to 0° C., in a solvent selected from the group consisting of acetonitrile (CH$_3$CN), methylene chloride (CH$_2$Cl$_2$), ethyl acetate, hexane, tetrahydrofuran (THF), tert-butyl methyl ether (TBME), dimethylformamide (DMF), dimethylsulfoxide (DMSO), ethylene glycol, a straight chain C$_1$-C$_5$ alcohol, and a branched C$_1$-C$_5$ alcohol, to obtain (rac)-3-keto-α-ionone.

56. A method comprising condensing (rac)-3-keto-α-ionone with (EtO)$_2$P(O)CH$_2$CN or (iso-PrO)$_2$P(O)CH$_2$CN in the presence of a base to obtain (7E,9E)-3-keto-α-ionylideneacetonitrile and (7E,9Z)-3-keto-α-ionylideneacetonitrile.

57. A method of preparing (3R,6R)-3-hydroxy-13-apo-ε-caroten-13-one and (3R)-3-hydroxy-13-apo-β-caroten-13-one comprising oxidatively degrading (3R,3'R,6'R)-lutein diacetate with tert-BuOOH (TBHP) and bleach, at a temperature ranging from −5° C. to room temperature (R.T.), in a solvent selected from the group consisting of acetonitrile (CH$_3$CN), methylene chloride (CH$_2$Cl$_2$), ethyl acetate, hexane, tetrahydrofuran (THF), tert-butyl methyl ether (TBME), dimethylformamide (DMF), dimethylsulfoxide (DMSO), a straight chain C$_1$-C$_5$ alcohol and a branched C$_1$-C$_5$ alcohol to obtain (3R,6R)-3-hydroxy-13-apo-ε-caroten-13-one and (3R)-3-hydroxy-13-apo-β-caroten-13-one.

58. A method of preparing a compound of the Formula XII and a compound of the Formula XIII comprising oxidatively degrading a compound having the Formula XI:

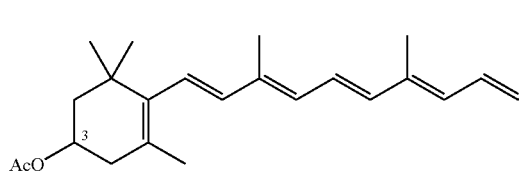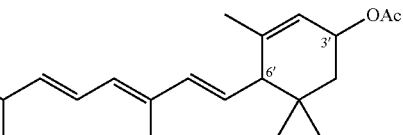

with an oxidizing agent, to obtain a compound of the Formula XII:

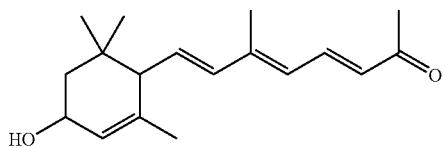

and a compound of the Formula XIII:

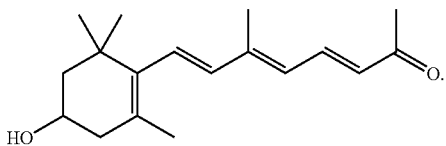

59. The method of claim 58, wherein said compound having the Formula (XI) is (3R,3'R,6'R)-lutein diacetate, (3R,3'S,6'S)-lutein diacetate, (3R,3'S,6'R)-lutein diacetate, (3R,3'R,6'S)-lutein diacetate, (3S,3'S,6'S)-lutein diacetate, (3S,3'R,6R)-lutein diacetate, (3S,3'R,6'S)-lutein diacetate, or (3S,3'S,6'R)-lutein diacetate, or a combination thereof.

60. The method of claim 56, wherein (3R,3'R,6'R)-lutein diacetate is oxidatively degraded with tert-BuOOH (TBHP) and bleach, at a temperature ranging from −5° C. to room temperature (R.T.), in a solvent selected from the group consisting of acetonitrile ($CH_3CN$), methylene chloride ($CH_2Cl_2$), ethyl acetate, hexane, tetrahydrofuran (THF), tert-butyl methyl ether (TBME), dimethylformamide (DMF), dimethylsulfoxide (DMSO), a straight chain $C_1$-$C_5$ alcohol and a branched $C_1$-$C_5$ alcohol to obtain (3R,6R)-3-hydroxy-13-apo-ε-caroten-13-one and (3R)-3-hydroxy-13-apo-β-caroten-13-one.

* * * * *